United States Patent
Taniguchi et al.

(10) Patent No.: US 12,012,616 B2
(45) Date of Patent: Jun. 18, 2024

(54) FORMATION OF THREE-DIMENSIONAL ORGAN FROM PLURIPOTENT STEM CELLS

(71) Applicant: Public University Corporation Yokohama City University, Kanagawa (JP)

(72) Inventors: Hideki Taniguchi, Yokohama (JP); Takanori Takebe, Yokohama (JP); Keisuke Sekine, Yokohama (JP)

(73) Assignee: Public University Corporation Yokohama City University, Kanagawa (JP)

( * ) Notice: Subject to any disclaimer, the term of this patent is extended or adjusted under 35 U.S.C. 154(b) by 791 days.

(21) Appl. No.: 16/768,019

(22) PCT Filed: Nov. 30, 2018

(86) PCT No.: PCT/JP2018/044144
§ 371 (c)(1),
(2) Date: May 28, 2020

(87) PCT Pub. No.: WO2019/107535
PCT Pub. Date: Jun. 6, 2019

(65) Prior Publication Data
US 2020/0362315 A1  Nov. 19, 2020

(30) Foreign Application Priority Data

Nov. 30, 2017  (JP) .................................. 2017-230647

(51) Int. Cl.
*C12N 5/071* (2010.01)
*A61L 27/36* (2006.01)
*C12N 5/074* (2010.01)

(52) U.S. Cl.
CPC ........ *C12N 5/0697* (2013.01); *A61L 27/3625* (2013.01); *A61L 27/3641* (2013.01); *C12N 5/0607* (2013.01); *A61L 2430/28* (2013.01); *C12N 2502/1358* (2013.01); *C12N 2502/28* (2013.01); *C12N 2506/03* (2013.01)

(58) Field of Classification Search
CPC .............. C12N 5/0697; C12N 2502/28; C12N 2502/14
See application file for complete search history.

(56) References Cited

U.S. PATENT DOCUMENTS

2014/0289877 A1* 9/2014 Taniguchi ............ C12N 5/0677
435/1.1

FOREIGN PATENT DOCUMENTS

| WO | 2013/047639 A1 | 4/2013 | |
|---|---|---|---|
| WO | WO-2013047639 A1 * | 4/2013 | ......... A01K 67/0271 |
| WO | 2017/110931 A1 | 6/2017 | |

OTHER PUBLICATIONS

Takebe et al., Massive and reproducible production of liver buds entirely from human pluripotent stem cells. Cell Reports, vol. 21, No. 10 (Dec. 5, 2017) pp. 2661-2670 (Year: 2017).*
International Search Report issued in corresponding International Patent Application No. PCT/JP2018/044144 dated Feb. 26, 2019.
Extended European Search Report issued in corresponding European Patent Application No. 18883756.1 dated Jul. 9, 2021.
Maguire et al., "Differentiation and Application of Induced Pluripotent Stem Cell-Derived Vascular Smooth Muscle Cells," Arteriosclerosis, Thrombosis, and Vascular Biology, 2026-2037 (2017).
Camp et al., "Multilineage communication regulates human liver bud development from pluripotency," Nature (2017).
Takebe et al., "Vascularized and functional human liver from an iPSC-derived organ bud transplant," Nature, 499: 481-485 (2013).
Takebe et al., "Generation of a vascularized and functional human liver from an iPSC-derived organ bud transplant," Nature Protocols, 9 (2): 396-409 (2014).
Takebe et al., "Vascularized and Complex Organ Buds from Diverse Tissues via Mesenchymal Cell-Driven Condensation," Cell Stem Cell, 16: 556-565 (2015).
Shinozawa et al., "Reverse engineering liver buds through self-driven condensation and organization towards medical application," Developmental Biology, 420: 221-229 (2016).
Handa et al., "Assembly of Human Organs from Stem Cells to Study Liver Disease," American Journal of Pathology, 184 (2): 348-357 (2014).
Takebe et al., "Massive and Reproducible Production of Liver Buds Entirely from Human Pluripotent Stem Cells." Cell Reports, 21: 2661-2670 (2017).

* cited by examiner

*Primary Examiner* — Kara D Johnson
(74) *Attorney, Agent, or Firm* — Morgan, Lewis & Bockius LLP

(57) ABSTRACT

The present invention solves the following problems [1] to [3] found in conventional methods of preparing a three dimensional structure (organ primordium) by coculturing functional cells with umbilical cord-derived vascular endothelial cells and bone marrow-derived mesenchymal cells: [1] the quality of resultant organ primordia varies greatly depending on donors; [2] the growth capacities of cell sources are limited; and [3] it is difficult to secure immunocompatibility because cells are derived from different sources. An organ bud prepared from vascular cells, mesenchymal cells and tissue or organ cells, wherein each of the vascular cell, the mesenchymal cell and the tissue or organ cell has been induced from pluripotent stem cells. A method of preparing an organ bud, comprising culturing vascular cells, mesenchymal cells and tissue or organ cells in vitro, wherein each of the vascular cell, the mesenchymal cell and the tissue or organ cell has been induced from pluripotent stem cells.

16 Claims, 15 Drawing Sheets

[Figure 1]
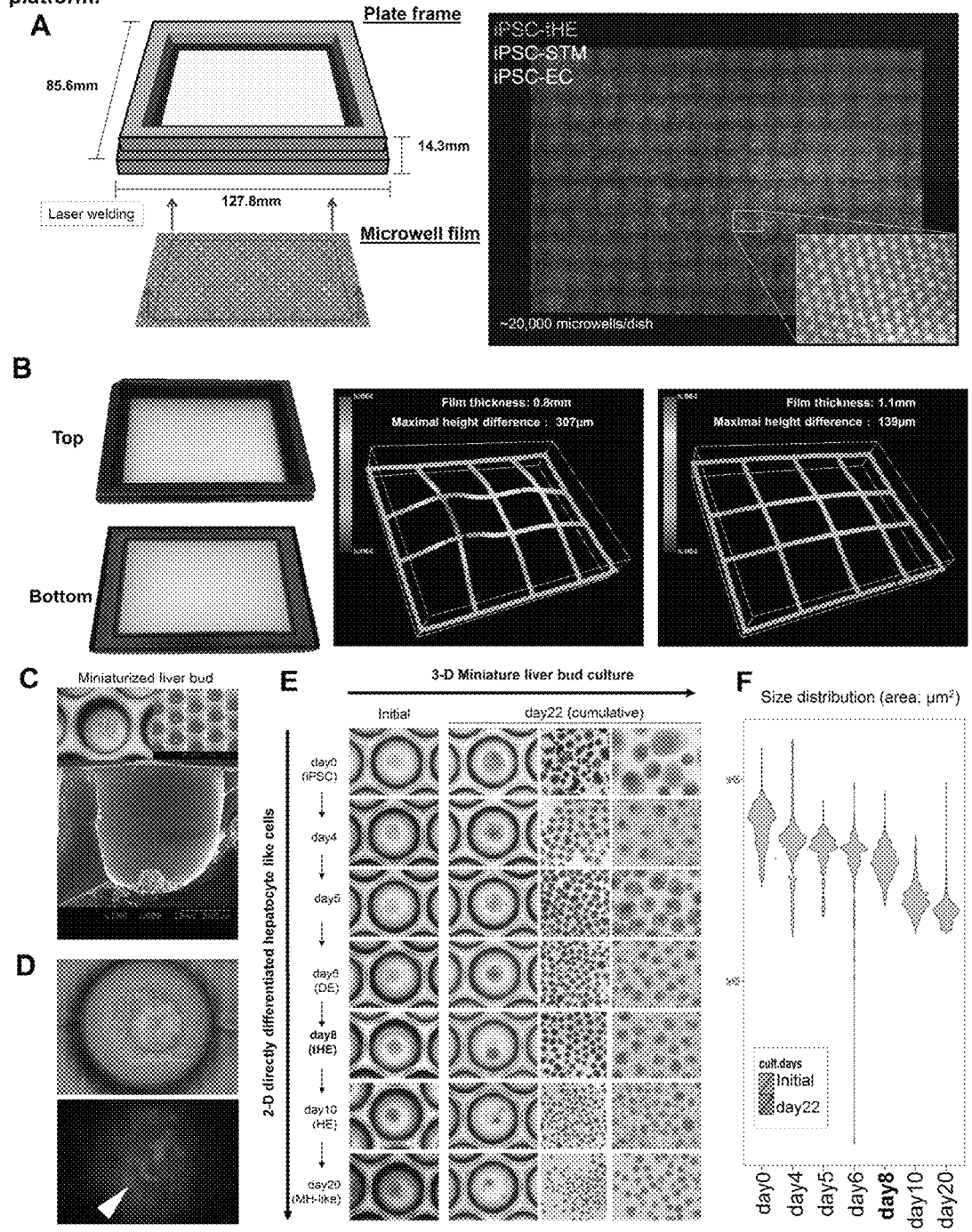

[Figure 2]
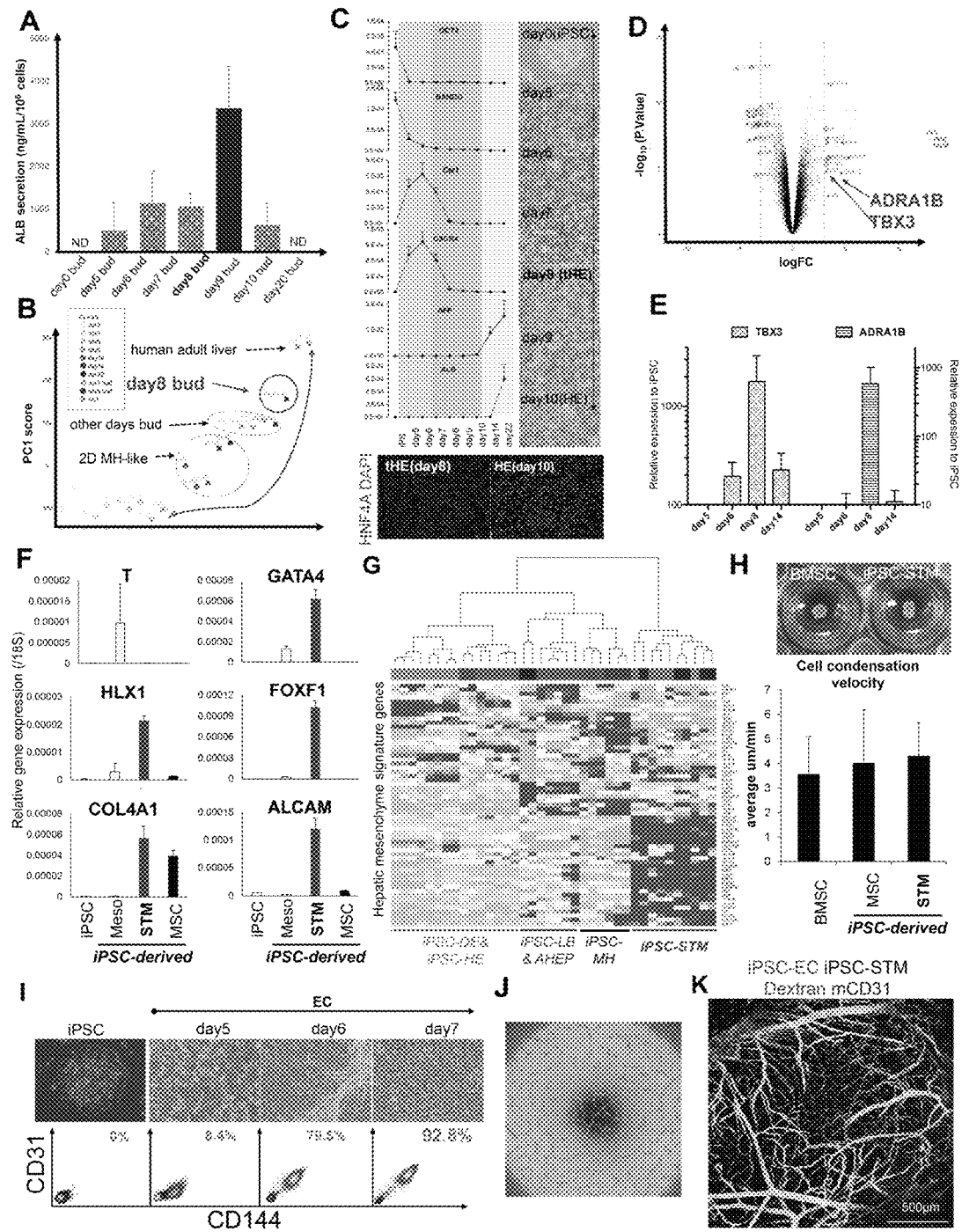

[Figure 3]
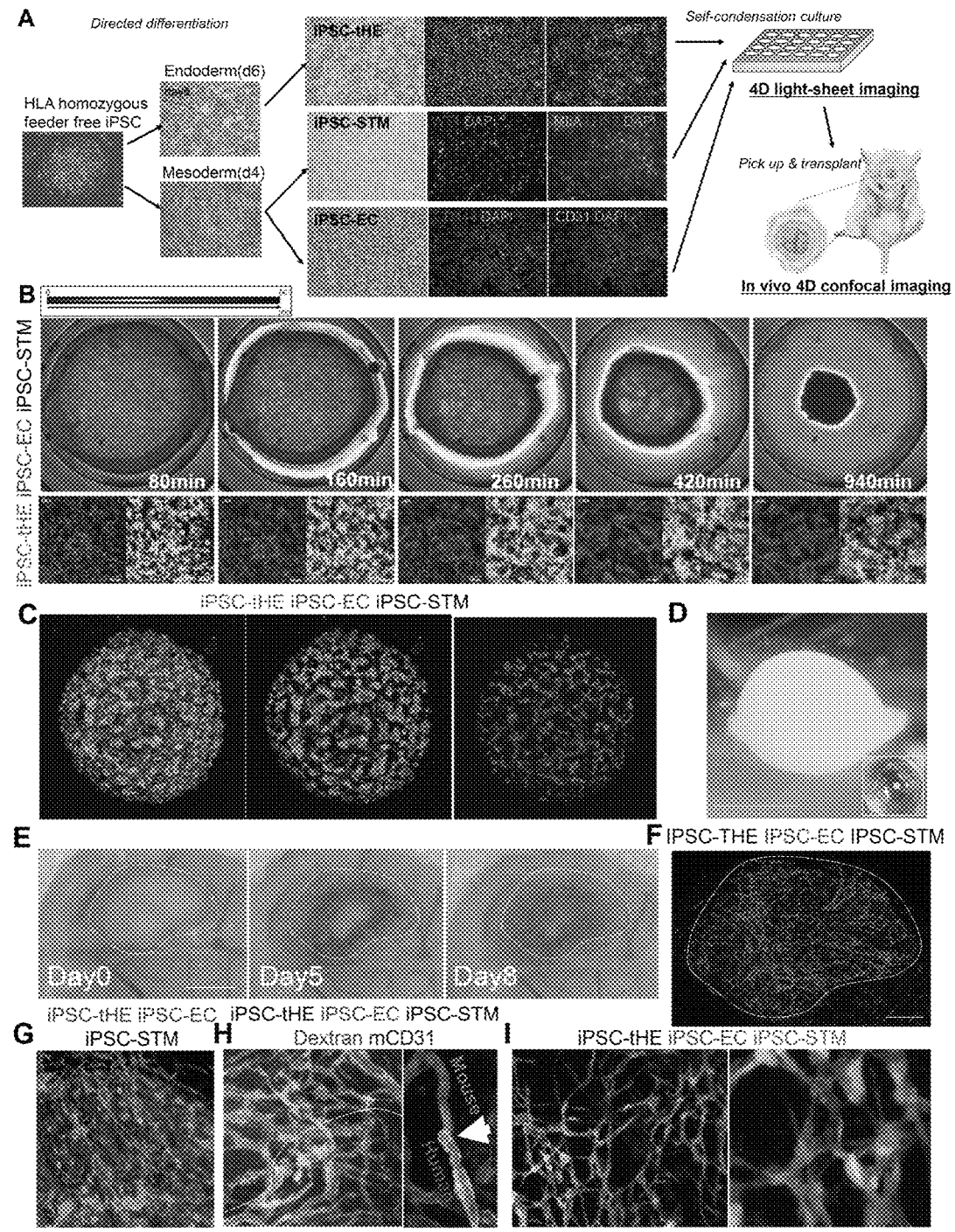

[Figure 4]
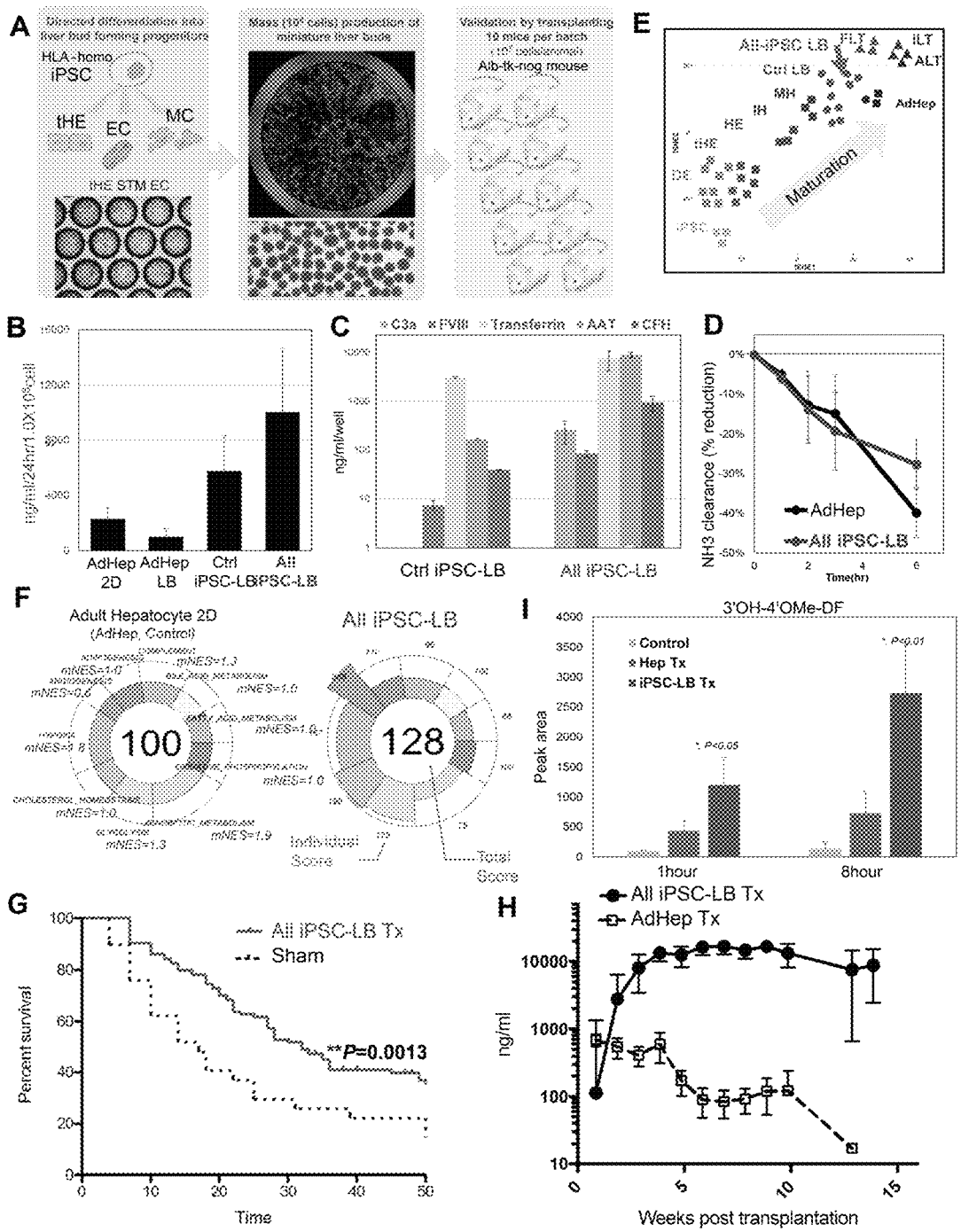
Figure 4. Functional validation of mass-produced miniaturized human liver buds

[Figure 5]
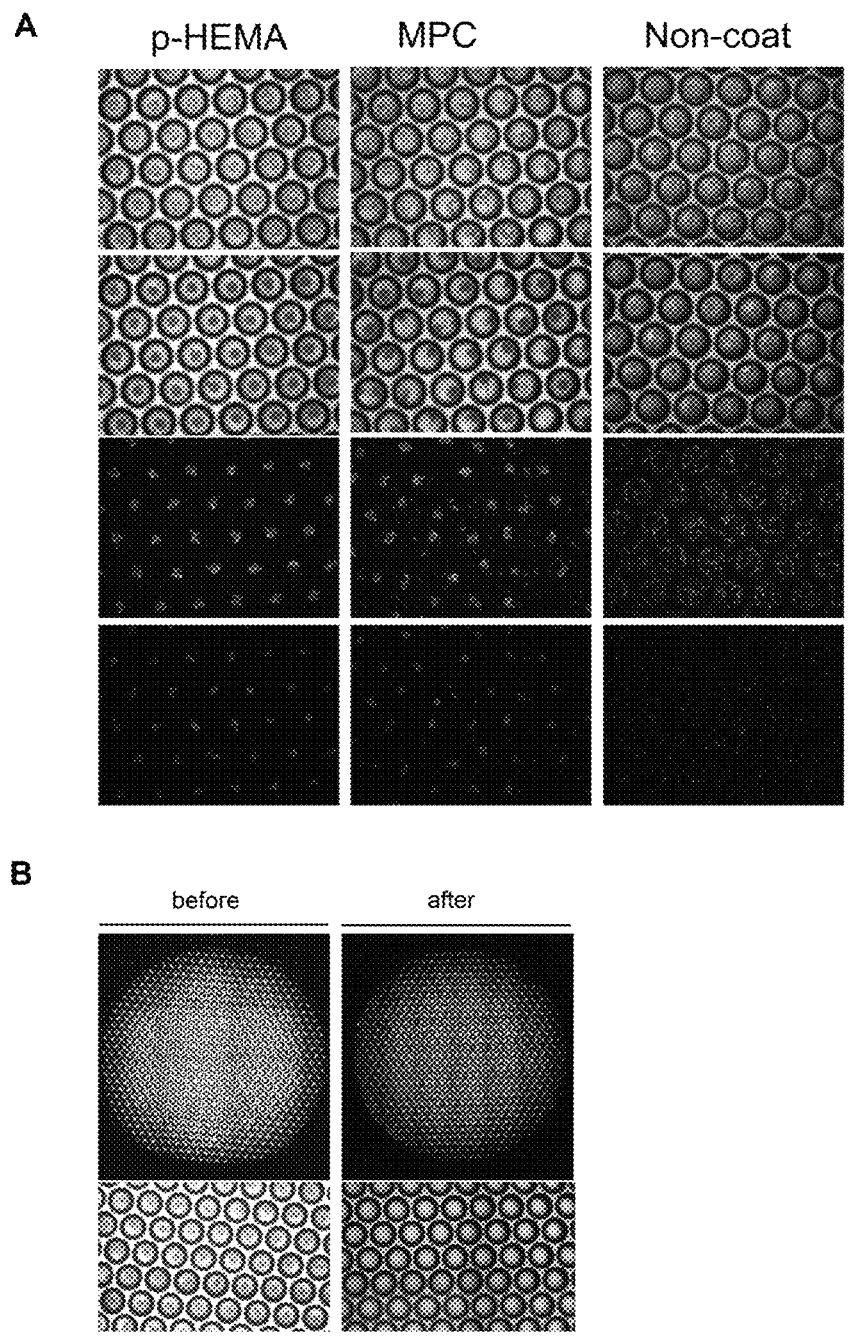

[Figure 6]
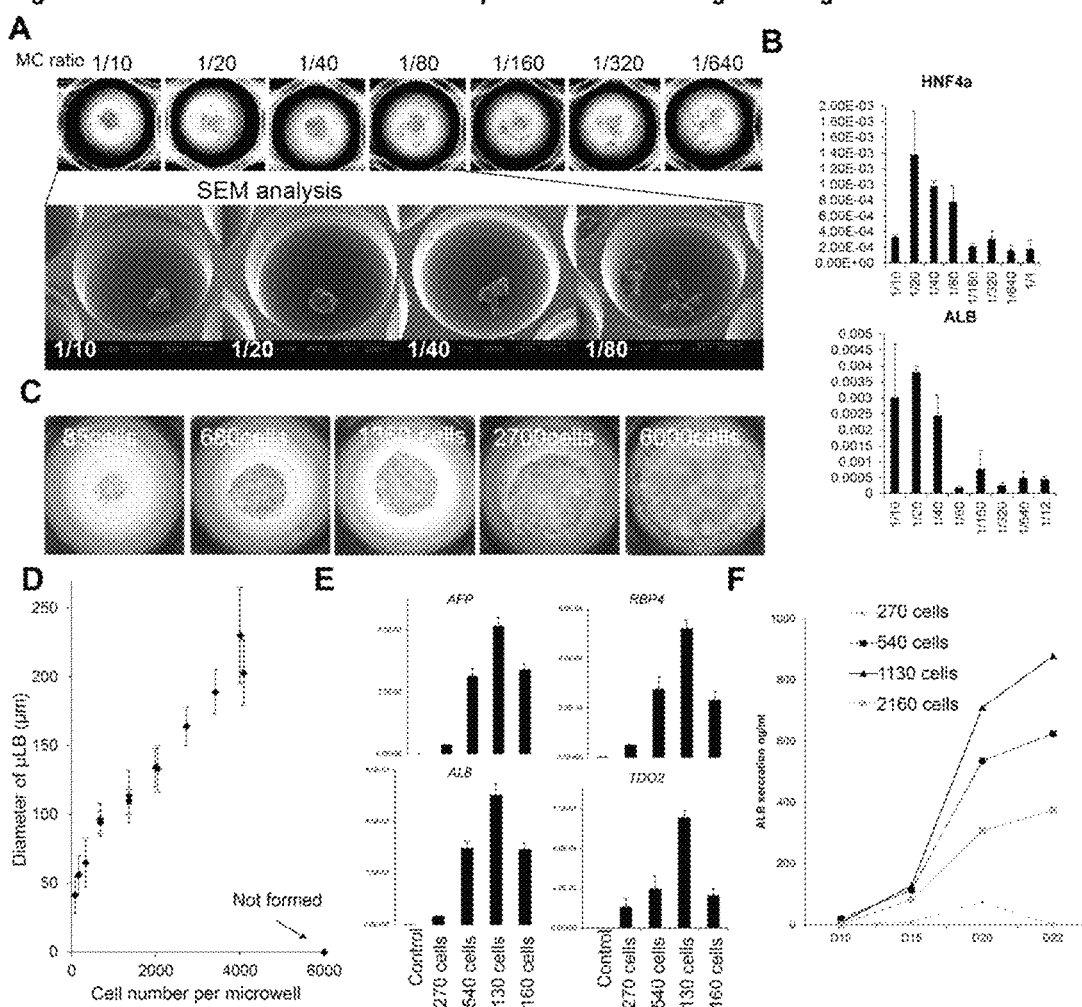

[Figure 7]
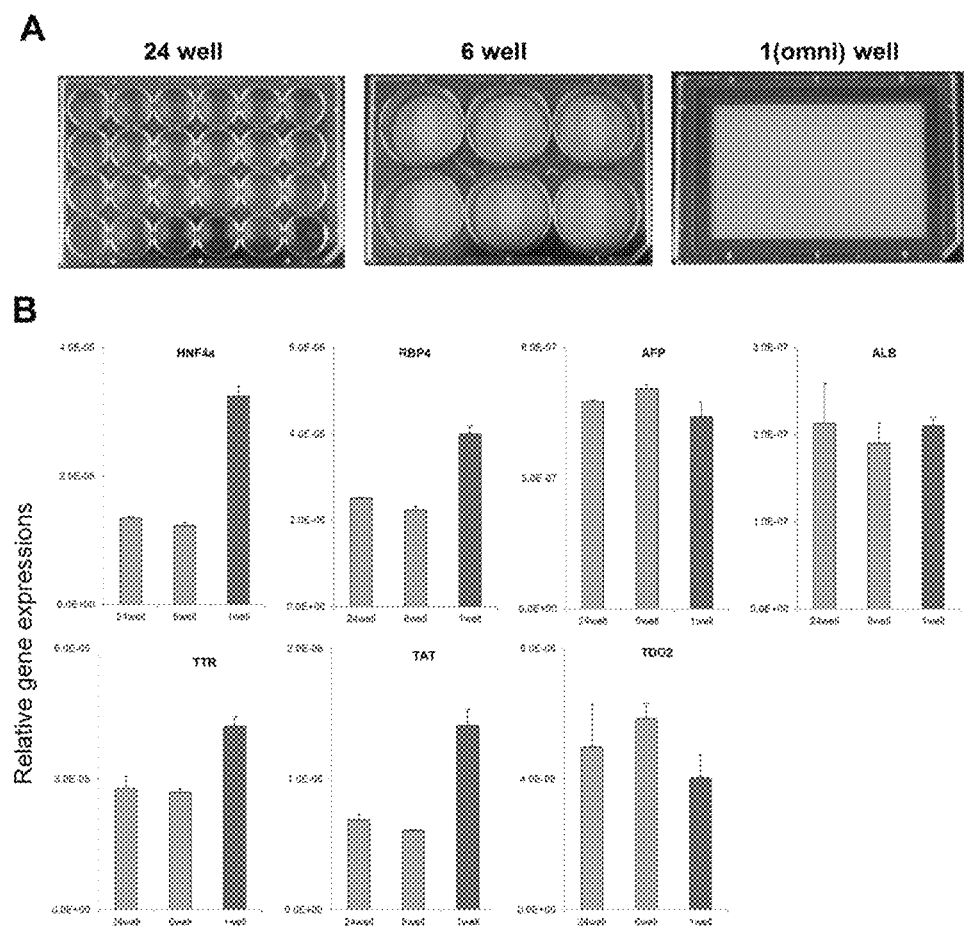

[Figure 8]
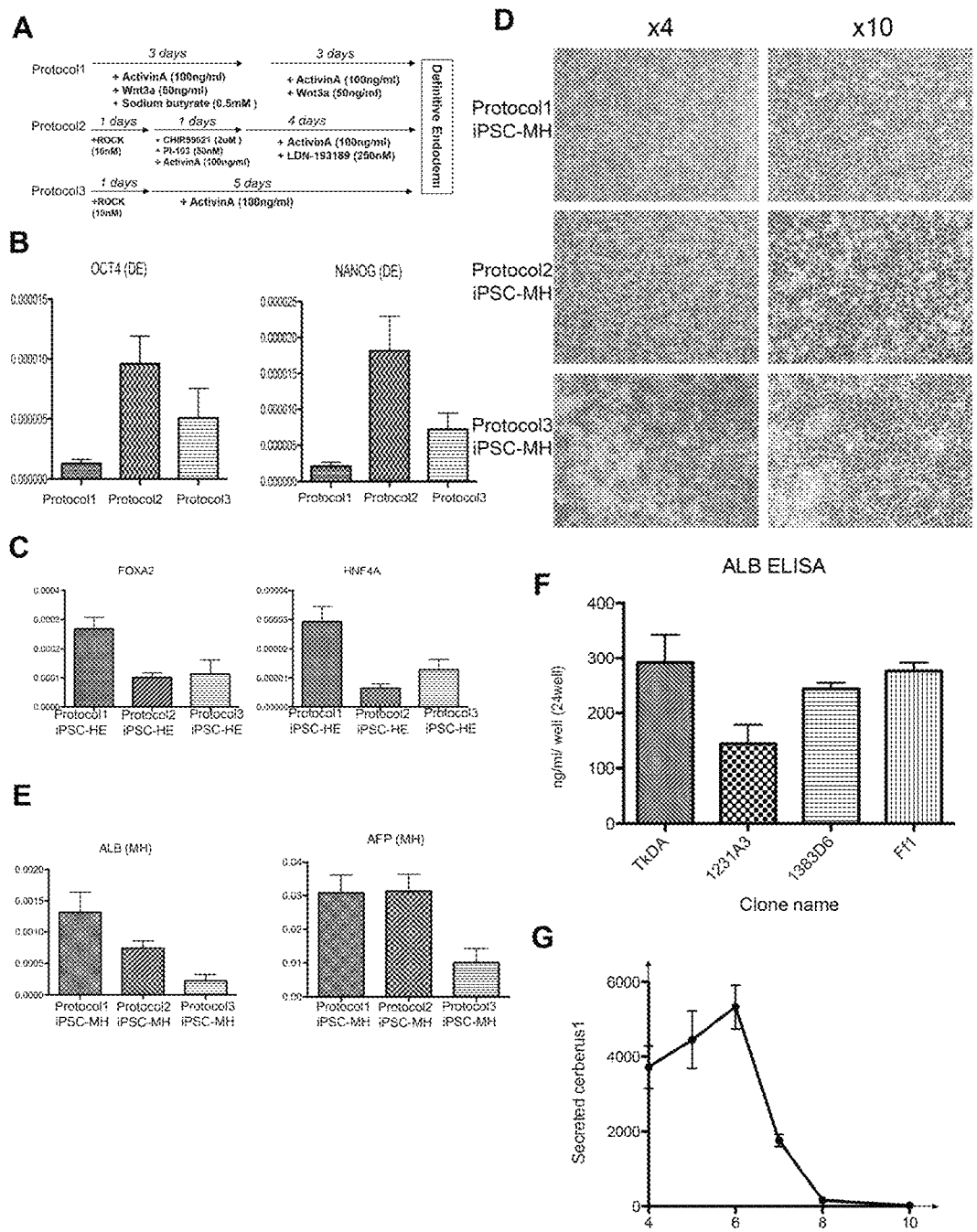

[Figure 9]
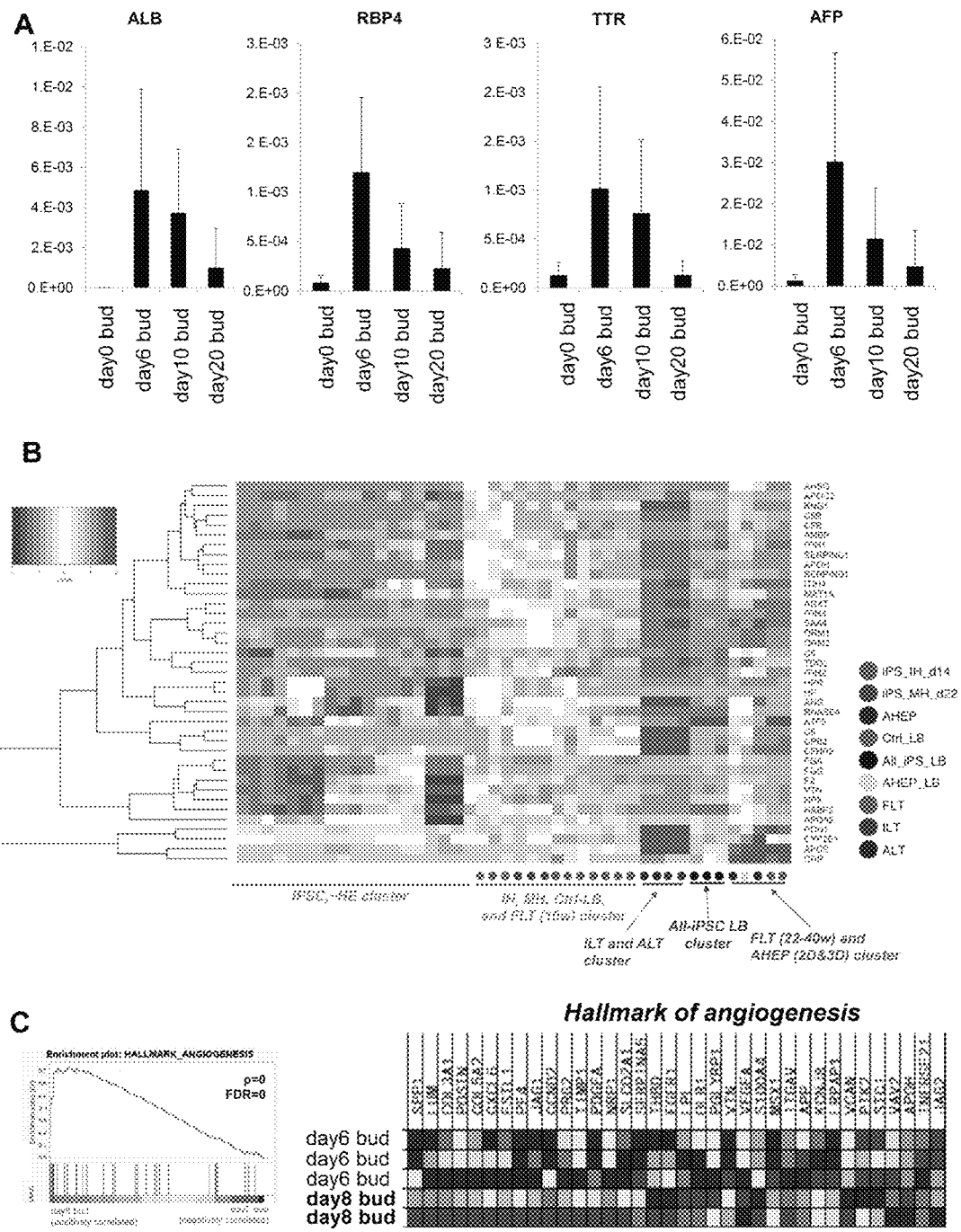

[Figure 10]
Figure S6 Identification of TBX3 and ADRA1B as a marker for iPSC-tHE
A
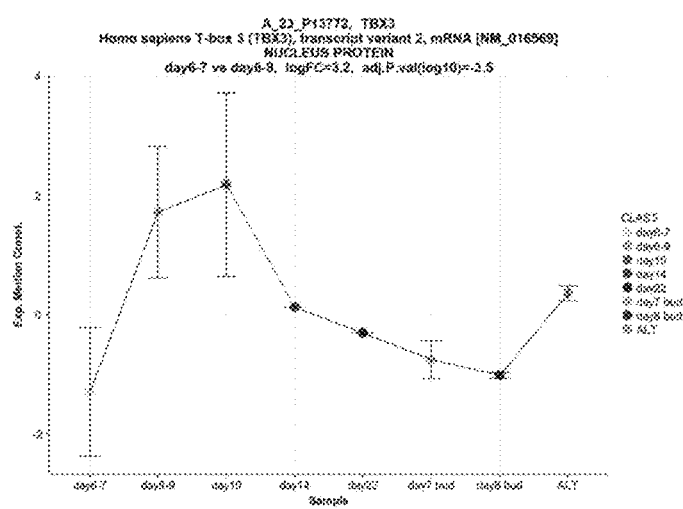
B
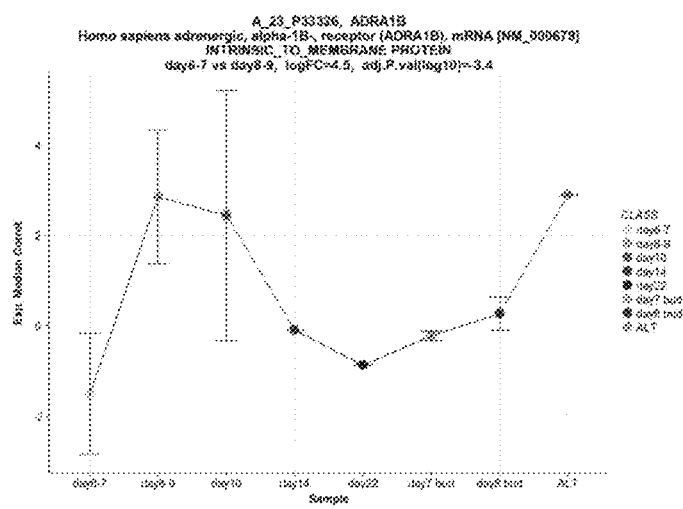

[Figure 11]
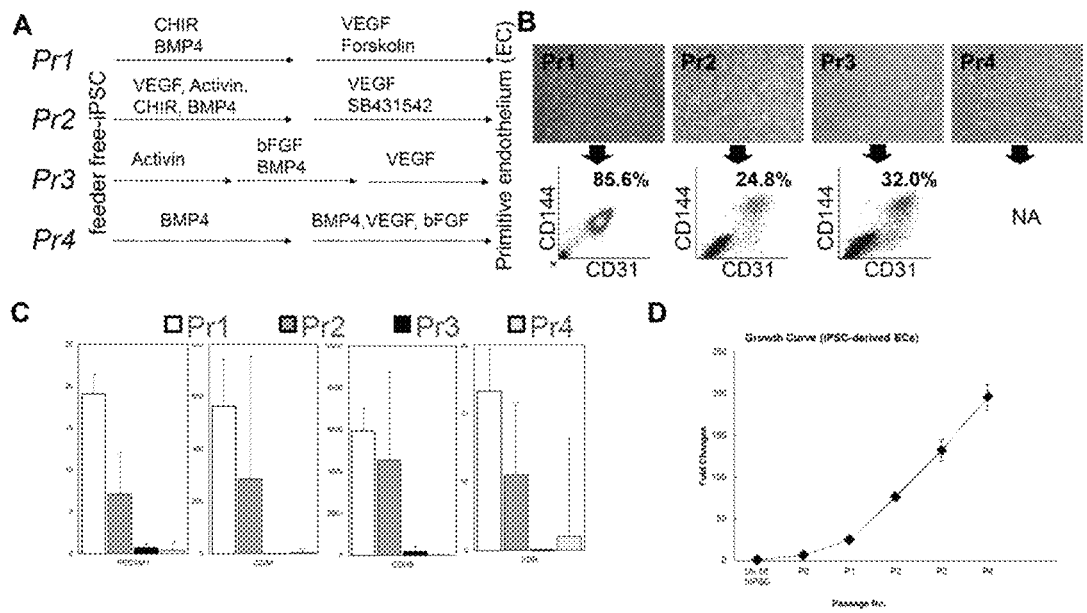
Figure S7. Highly efficient differentiation into primitive endothelial progenitors from feeder free human iPSC
[Figure 12]
Figure S8. In vivo functionalization of human iPSC liver buds.
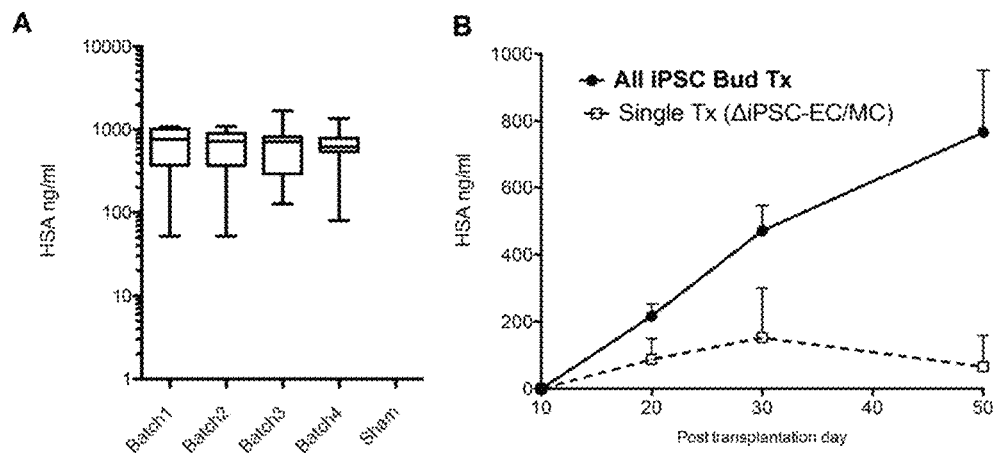

Revised Method

FORMATION OF THREE-DIMENSIONAL ORGAN FROM PLURIPOTENT STEM CELLS

TECHNICAL FIELD

The present invention relates to construction of three-dimensional organs from pluripotent stem cells.

BACKGROUND ART

The preset inventors have developed a method of preparing three-dimensional tissues (organ primordia) by mixing functional cells used in regenerative medicine, etc. (such as pluripotent stem cell-derived organ cells) with umbilical cord-derived vascular endothelial cells and bone marrow-derived mesenchymal cells; and reported that organ primordia prepared by this method are superior to those cells obtained by directed differentiation under plane culture, in terms of function in vitro and therapeutic effects for disease model animals (Non-Patent Document No. 1: Nature 2013; Non-Patent Document No. 2: Cell Stem Cell 2015; Patent Documents Nos. 1 and 2).

PRIOR ART LITERATURE

Non-Patent Documents

Non-Patent Document No. 1: Takebe T et al., Nature 499, pp 481-484, 2013
Non-Patent Document No. 2: Takebe T et al., Cell Stem Cell 16, pp 556-565, 2015

Patent Documents

Patent Document No. 1: WO2013/047639
Patent Document No. 2: WO2015/012158

DISCLOSURE OF THE INVENTION

Problem for Solution by the Invention

Conventional methods using two types of cells, one derived from umbilical cord and the other from bone marrow, have the following problems which are ultimate challenges for practical application: (1) the quality of resultant organ primordia varies greatly depending on donors; (2) the growth capacities of cell sources are limited; and (3) it is difficult to secure immunocompatibility because cells are derived from different sources. Moreover, since umbilical cord/bone marrow-derived cells are highly matured cells, they greatly differ in differentiation stage from the immature cells required for generation of organ primordia, and largely depart from the scenario of in vivo development.

Means to Solve the Problem

The present inventors have succeeded in preparing organ primordia from differentiation stage-synchronized multiple immature cells by ensuring that all three cell species used to prepare three-dimensional organ primordia are made from induced pluripotent stem cells (iPS cells). Specifically, the present inventors have prepared human liver buds using a combination of iPS cell-derived hepatic endoderm cells, iPS cell-derived vascular endothelial cells and iPS cell-derived mesenchymal cells, and compared them with those human liver buds which are prepared by conventional methods using a combination of iPS cell-derived hepatic endoderm cells, umbilical cord-derived vascular endothelial cells and bone marrow-derived mesenchymal cells, in terms of in vitro albumin secretion capacity, gene expression of differentiation markers, and so on. As a result, a remarkable improvement of function was recognized compared with the liver buds prepared by conventional methods. Further, when liver buds equivalent to $6 \times 10^6$ iPS cell-derived hepatic endoderm cells were transplanted into immunodeficient animal (NOD/scid mouse), the same result was obtained from the human albumin level secreted into the serum. According to the present invention, it becomes possible to achieve a remarkable improvement of function and also to reduce cost and labor required for quality evaluation and production. It is highly probable that similar effects will be obtained by replacing iPS cells with other pluripotent stem cells (e.g., embryonic stem (ES) cells).

A summary of the present invention is as described below.
(1) An organ bud prepared from vascular cells, mesenchymal cells and tissue or organ cells, wherein each of the vascular cell, the mesenchymal cell and the tissue or organ cell has been induced from pluripotent stem cells.
(2) The organ bud of (1) above, which is a structure capable of differentiating into an organ through maturing.
(3) The organ bud of (1) or (2) above, wherein the pluripotent stem cell is derived from human.
(4) The organ bud of any one of (1) to (3) above, wherein the pluripotent stem cell is at least one cell selected from the group consisting of induced pluripotent stem cell and embryonic stem cell.
(5) The organ bud of any one of (1) to (4) above, wherein the organ cell is hepatocyte and the organ bud is liver bud.
(6) The organ bud of (5) above, wherein the hepatocyte is TBX3 positive and ADRA1B positive.
(7) The organ bud of any one of (1) to (6) above, wherein the mesenchymal cell is CD166 positive and CD31 negative.
(8) The organ bud of any one of (1) to (7) above, wherein the mesenchymal cell is LHX2 positive and WT1 positive.
(9) The organ bud of (8) above, wherein the transcriptions of FOXF1, HLX1, COL4A and ALCAM of the mesenchymal cell are activated and the mesenchymal cell is LHX2 positive, WT1 positive and MIIA positive.
(10) The organ bud of any one of (1) to (9) above, wherein the vascular cell is CD31 positive and CD144 positive.
(11) The organ bud of (10) above, wherein expression of at least one gene selected from the group consisting of PECAM1, CDH5, KDR and CD34 of the vascular cell is increased relative to the corresponding expression in the pluripotent stem cell before directed differentiation.
(12) The organ bud of any one of (1) to (11) above, wherein TBX3 and ADRA1B co-positive cells obtained through the following steps are used as tissue or organ cells:
  a) culturing pluripotent stem cells in the presence of a ROCK inhibitor and then in the presence of a factor belonging to the transforming growth factor β family, a factor belonging to the Wnt family and a class I histone deacetylase (HDAC) inhibitor, and further culturing the cells in the presence of a factor belonging to the transforming growth factor β family and a factor belonging to the Wnt family, and
  b) culturing the resultant cells from the above step in the presence of an FGF and a factor belonging to the TGF-β superfamily for directed differentiation into TBX3 and ADRA1B co-positive cells.
(13) The organ bud of any one of (1) to (11) above, wherein TBX3 and ADRA1B co-positive cells obtained through the following steps are used as tissue or organ cells:

a) culturing pluripotent stem cells in the presence of a ROCK inhibitor and then in the presence of a β catenin activator, a PI3K inhibitor and a factor belonging to the transforming growth factor β family, and further culturing the cells in the presence of a factor belonging to the transforming growth factor β family and a BMP inhibitor, and b) culturing the resultant cells from the above step in the presence of an FGF and a factor belonging to the TGF-β superfamily for directed differentiation into TBX3 and ADRA1B co-positive cells.

(14) The organ bud of any one of (1) to (11) above, wherein TBX3 and ADRA1B co-positive cells obtained through the following steps are used as tissue or organ cells:

a) culturing pluripotent stem cells in the presence of a ROCK inhibitor and then in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(15) The organ bud of any one of (1) to (12) above, wherein TBX3 and ADRA1B co-positive cells obtained through the following steps are used as tissue or organ cells:

a) culturing pluripotent stem cells in the presence of a ROCK inhibitor and then in the presence of a factor belonging to the transforming growth factor β family and a β catenin activator, and further culturing the cells in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(16) The organ bud of any one of (1) to (15) above, wherein LHX2 and WT1 co-positive cells obtained through the following steps are used as mesenchymal cells:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, and c) further culturing the cells in the presence of an FGF.

(17) The organ bud of any one of (1) to (15) above, wherein CD166 positive but CD31 negative cells obtained through the following steps are used as mesenchymal cell:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, c) further culturing the cells in the presence of an FGF, and d) subsequently conducting maintenance culture of the cells in a medium for mesenchymal cells.

(18) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a β catenin activator and a factor belonging to the TGF-β superfamily, and c) further culturing the cells in the presence of a vascular endothelial growth factor receptor (VEGFR) agonist and an adenylate cyclase activator.

(19) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a VEGFR agonist, a factor belonging to the transforming growth factor β family, a β catenin activator and a factor belonging to the TGF-β superfamily, and c) further culturing the cells in the presence of a VEGFR agonist and an inhibitor of TGF-β type I receptor.

(20) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a factor belonging to the transforming growth factor β family, c) further culturing the cells in the presence of an FGF and a factor belonging to the TGF-β superfamily, and d) subsequently culturing the cells in the presence of a VEGFR agonist.

(21) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a factor belonging to the TGF-β superfamily, and c) further culturing the cells in the presence of a factor belonging to the TGF-β superfamily, a VEGFR agonist and an FGF.

(22) A method of preparing an organ bud, comprising culturing vascular cells, mesenchymal cells and tissue or organ cells in vitro, wherein each of the vascular cell, the mesenchymal cell and the tissue or organ cell has been induced from pluripotent stem cells.

(23) The method of (22) above, wherein the cells are cultured without using scaffold materials.

(24) A method of preparing a tissue or an organ, comprising transplanting the organ bud of any one of (1) to (21) above into a non-human animal and differentiating the organ bud into a tissue or an organ.

(25) A method of transplanting an organ bud, comprising transplanting the organ bud of any one of (1) to (21) above into a human or a non-human animal.

(26) A method of regeneration or function recovery of a tissue or an organ, comprising transplanting the organ bud of any one of (1) to (21) above into a human or a non-human animal and differentiating the organ bud into a tissue or an organ.

(27) A method of preparing a non-human chimeric animal, comprising transplanting the organ bud of any one of (1) to (21) above into a non-human animal and differentiating the organ bud into a tissue or an organ.

(28) A method of evaluating a drug, comprising using at least one member selected from the group consisting of the organ bud of any one of (1) to (21) above, the tissue or organ prepared by the method of (24) above and the non-human chimeric animal prepared by the method of (27) above.

(29) A method of preparing TBX3 and ADRA1B co-positive cells, comprising:

a) culturing pluripotent stem cells in the presence of a ROCK inhibitor and then in the presence of a factor belonging to the transforming growth factor β family, a factor belonging to the Wnt family and a class I histone deacetylase (HDAC) inhibitor, and further culturing the cells in the presence of a factor belonging to the transforming growth factor β family and a factor belonging to the Wnt family, and b) culturing the resultant cells from the above step in the presence of an FGF and a factor belonging to the TGF-β superfamily for directed differentiation into TBX3 and ADRA1B co-positive cells.

(30) A method of preparing TBX3 and ADRA1B co-positive cells, comprising:

a) culturing pluripotent stem cells in the presence of a ROCK inhibitor and then in the presence of a β catenin activator, a PI3K inhibitor and a factor belonging to the transforming growth factor β family, and further culturing the cells in the presence of a factor belonging to the transforming growth factor β family and a BMP inhibitor, and b) culturing the resultant cells from the above step in the presence of an FGF and a factor belonging to the TGF-β superfamily for directed differentiation into TBX3 and ADRA1B co-positive cells.

(31) A method of preparing TBX3 and ADRA1B co-positive cells, comprising:

a) culturing pluripotent stem cells in the presence of a ROCK inhibitor and then in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(32) A method of preparing TBX3 and ADRA1B co-positive cells, comprising:

a) culturing pluripotent stem cells in the presence of a ROCK inhibitor and then in the presence of a factor belonging to the transforming growth factor β family and a β catenin activator, and further culturing the cells in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(33) A method of preparing LHX2 and WT1 co-positive cells, comprising:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, and c) further culturing the cells in the presence of an FGF.

(34) A method of preparing CD166 positive but CD31 negative cells, comprising:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, c) further culturing the cells in the presence of an FGF, and d) subsequently conducting maintenance culture of the cells in a medium for mesenchymal cells.

(35) A method of preparing CD31 and CD144 co-positive cells, comprising:

a) culturing pluripotent stem cells in the presence of a ROCK inhibitor, b) then culturing the cells in the presence of a β catenin activator and a factor belonging to the TGF-β superfamily, and c) further culturing the cells in the presence of a vascular endothelial growth factor receptor (VEGFR) agonist and an adenylate cyclase activator.

(36) A method of preparing CD31 and CD144 co-positive cells, comprising:

a) culturing pluripotent stem cells in the presence of a ROCK inhibitor, b) then culturing the cells in the presence of a VEGFR agonist, a factor belonging to the transforming growth factor β family, a β catenin activator and a factor belonging to the TGF-β superfamily, and c) further culturing the cells in the presence of a VEGFR agonist and an inhibitor of TGF-β type I receptor.

(37) A method of preparing CD31 and CD144 co-positive cells, comprising:

a) culturing pluripotent stem cells in the presence of a ROCK inhibitor, b) then culturing the cells in the presence of a factor belonging to the transforming growth factor β family, c) further culturing the cells in the presence of an FGF and a factor belonging to the TGF-β superfamily, and d) subsequently culturing the cells in the presence of a VEGFR agonist.

(38) A method of preparing CD31 and CD144 co-positive cells, comprising:

a) culturing pluripotent stem cells in the presence of a ROCK inhibitor, b) then culturing the cells in the presence of a factor belonging to the TGF-β superfamily, and c) further culturing the cells in the presence of a factor belonging to the TGF-β superfamily, a VEGFR agonist and an FGF.

Effect of the Invention

The method of the present invention is advantageous over the conventional method using the two types of cells, one derived from umbilical cord and the other from bone marrow, in the following points: (1) the resultant organ primordia are stable in quality because of being non-donor dependent, (2) organ primordia generated from three types of cells that are entirely derived from iPS cells are dramatically superior to conventional ones in functionality and (3) it becomes easy to secure immunocompatibility.

The present specification encompasses the contents disclosed in the specification and/or drawings of Japanese Patent Application No. 2017-230647 based on which the present patent application claims priority.

BRIEF DESCRIPTION OF THE DRAWINGS

FIG. 1 (FIG. 1) Scalable liver bud production and differentiation by developing an omni-well-array platform.

Figure 13:
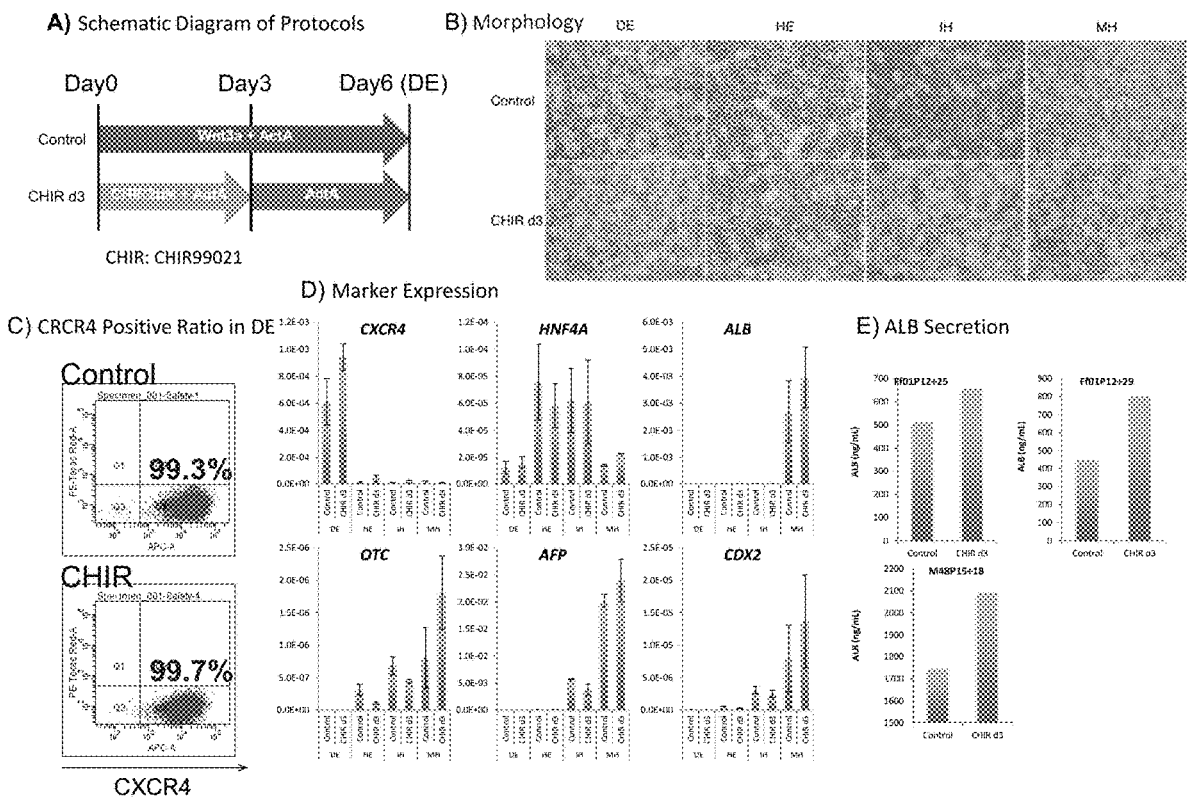

(A) The schematic design (middle) of an omni-well-array plate for mass production. Fluorescent image analysis (right) confirms the large-scale (>20,000) production of micro liver buds (LBs) entirely from human iPSCs. (B) The appearance of 1 (omni)-well-array plate (left), and plate flatness (right) as shown by a 3D profilometer. (C) SEM image of iPSC-LBs generated from triple progenitor co-culture. (D) Confocal image of the generated iPSC-LB revealed endothelial sprouting (white arrowhead) inside. Green, iPSC-HE; red, HUVEC. (E) Gross morphologies of LBs generated from different endoderm stages (days 0-20). The x axis shows 3D culture duration (cumulative), and the y axis shows the source cell stage from 2D culture. The right two columns show low- and high-magnification images after collection at day 22. (F) Violin plot analysis of the size homogeneity in various endoderm-derived LBs. Data were collected by quantification of the morphology of over 600 LBs at cumulative day 22 relative to the first day of 3D culture.

FIG. 2 (FIG. 2) Reverse optimization of human iPSC-derived liver bud-forming multiple progenitors.
(A) ELISA-based quantification of time-course-dependent AFP and ALB production per 24 hr/$2\times10^5$cells at day 20. Data represent means±SD, n=4; *p<0.05. (B) Principal-component analysis of LBs generated from endodermal cells of multiple stages revealed a significant commitment toward the hepatic fate. The x axis reflects in vitro experiment-based maturity order. (C) Characterization of each differentiation-stage-specific reported marker by qRT-PCR analysis of pluripotency, definitive endoderm, and HE cell markers. The microscopic morphology of cells at various stages is presented in the right panel. The bottom panel shows immunostaining of HNF4A at the day 8 and day 10 stages. (D) Volcano plot gene expression data. Genes differentially expressed at a log2-fold change level between day 6 and day 8 stage >3 with a p value<0.05 are displayed as red circles. Cell surface proteins or nuclear proteins are indicated by red circles with each gene name in bold letter. (E) Day 8 transitional endodermal cells are marked by both TBX3 and ADRA1B and proteins by immunostaining (see FIG. 3A). Data represent the means±SD, n=3; *p<0.05. (F) qRT-PCR-based screen of the early mesoderm gene T (BRACHURY) and the STM genes HLX1, GATA4, FOXF1, COL4A1, and ALCAM. Meso, day 3 iPSC-derived lateral plate mesoderm; STM, day 10 cells after FGF2 and PDGFB co-exposure; MSC, day 20 cells maintained in MSC medium after passaging STM. Error bars represent the SD of values obtained from three independent experiments (n=4). (G) Hierarchical clustering with adult human hepatic (AdHep) mesenchymal cell signatures in iPSC-STM (Asahina et al., 2009, Asahina et al., 2011, El Taghdouini et al., 2015). (H) Time-lapse imaging analysis of the self-condensation from iPSC-STM by phase contrast microscopy. The velocity of collective cell movement is presented as an average of 3 independent experiments. Two-day-cultured tissues using BMSCs and iPSC-MSC are shown as controls. (I, J) Microscopic characterization of iPSC-EC and FACS-based quantification of CD31 and CD144 over time (I) and subsequent endothelial sprouting assay on Matrigel (J). (K) Generation of human vascular networks in vivo by co-transplantation of iPSC-STM and AAVS1::mCherry iPSC-ECs. Dextran, green; mouse-specific CD31, blue. Scale bar, 500 μm.

FIG. 3 (FIG. 3) Self-organization of human liver buds entirely from iPSC-derived multiple progenitors.
(A) Overview of the protocol used for all-iPSC LB generation from feeder-free human iPSCs. Process verification was routinely conducted by immunostaining of TBX3 (red) and ADRA1B (red) on tHE cells; WT1 (red), LHX2 (red), and myosin HA (green) in STM; and CD144 (red) and CD31 (green) on ECs, respectively. (B) Self-organization into LBs with endothelial sprouting after 72 hr of culture was confirmed by bright field (top) and light-sheet (bottom) 4D time-lapse imaging, respectively. Green, iPSC-tHE; red, iPSC-EC; not labeled, iPSC-STM. Scale bar, 500 μm. (C) Confocal imaging of the entire all-iPSC buds confirmed the presence of an endothelial network. (D) Macroscopic lateral view of generated all-iPSC buds. The panel shows a top view. Scale bar, 1,000 μm. (E) Gross observation of transplanted all-iPSC-LBs showing perfusion of human blood vessels at day 2. The dotted area indicates the transplanted all-iPSC-LBs. (F) Intravital imaging of transplanted all-iPSC-LBs demonstrating the formation of human blood vessels from iPSC-ECs. Red, AAVS1::mCherry iPSC-ECs. Scale bar, 500 μm. (G) Presence of iPSC-hepatic cells aligned with human-iPSC-derived vessels inside all-iPSC-LB transplants at day 28. Green, iPSC-tHEs; red, iPSC-ECs. (H) Dextran and fluorescent mouse CD31 antibody co-infusion study revealing the connections (white dotted line or arrow) among iPSC-ECs and host mouse vessels. Green, dextran; red, iPSC-ECs; blue, mouse CD31. (I) Close association between iPSC-STM and iPSC-EC. Green, iPSC-STM; red, iPSC-EC.

FIG. 4 (FIG. 4) Functional validation of mass-produced miniaturized human liver buds.
(A) Strategic batch validation scheme on each $10^8$-cell-scale production cycle by assessing in vitro and in vivo function. The middle panel shows the uniformity of collected LB morphology. Green, iPSC-tHEs. (B) Albumin production in differentiated all iPSC-LBs. As controls, human adult hepatocytes in 2D (AdHep 2D), AdHep coculture (AdHep LB), and control LB (generated from iPSC-tHEs, HUVECs, and BMSCs) are shown. Data represent means±SD, n=6. (C) Multiple-hepatocyte-derived protein production and (D) ammonia metabolism of in-vitro-cultured all-iPSC-LBs at day 21 of culture. Data represent means±SD, n =6 (C) and n=3 (D). (E) tSNE-based visualization of hepatic maturation status of LBs generated entirely from iPSC (all iPSC-LB) compared with previous approaches and human primary samples. (F) APRES profiles between human adult hepatocytes (F) and differentiated all iPSC-LB (G) shown by aster plot. (G) Kaplan-Meier survival curves of transplanted and sham groups in a subacute liver failure model using alb-Tk-NOG mouse. n=114 for LB and n=39 for the sham-transplanted group. **p=0.0013. X axis indicates post-transplant day. (H) Time-dependent human serum albumin production in the all-iPSC-LB transplant (n=48) or human adult hepatocyte transplant (n=12). Data represent means±SEM. (I) Detection of human-specific diclofenac metabolite in iPSC-LB transplanted mice. 3'-Hydroxy-4'-methoxydiclofenac (VI), which is a human-specific metabolite known to accumulate in the plasma, was quantified by liquid chromatography/tandem mass spectrometry (LC-MS/MS).

FIG. 5 (FIG. S1) Coating optimization and collection of mass produced LBs.
(A) Coating with pHEMA and MPC polymers prior to cell seeding. Green, HUVEC; Red, MSC. (B) Collection of LBs by pipetting. Microscopic views acquired before (left) and after (right) LB collection are shown. After collection, no remaining LBs were detected, suggesting successful collection of LBs from the plate.

FIG. 6 (Figure S2) Studies of cell dose- and mixture ratio-dependency for generating LBs.
(A) Various proportions of mesenchymal cells (MCs) were examined for LB generation on the Elplasia platform. Microscopic and electron microscopic views are shown. A number of generated LBs were shown in the indicated MC proportions. (B) qRT-PCR analysis of HNF4A and ALB revealed that $\frac{1}{20}$ of total cells is most efficient for liver bud generation. The data represent means±s.d., n=3. (C, D) Total cell-dependent increase in the diameter of LBs, up to 4000 cells per spot. Cells didn't form a tissue at 6000 cells per spot. Green, HUVEC; Red, MSC. The quantification of LB size is presented in D. (E) Gene expression and (F) protein production capacity of LBs at each indicated cell dose. The data represent means±s.d., n=3.

FIG. 7 (Figure S3) Establishment of the omni-well plate for large-scale production. (A) Elplasia 24 well, 6 well, and 1(omni) well plate. All the plates meet SBS footprint dimensions. By minimizing dead space, the number of microwells per plate increased as follows: 14,400 (600×24 well), 18,000 (3,000×6 well) and 20,000 (1 well). (B) qRT-PCR analysis of the hepatic marker genes HNF4A, RBP4, AFP, ALB, TTR, TAT, TDO2 and GLUT2 in LBs derived from 24 well, 6 well and omni (1) well plate. The data represent means±s.d., n=3.

FIG. 8 (Figure S4) Optimization of the iPSC-derived endodermal cell induction protocol.
(A) Three representative protocols for generating definitive endoderm cells. (B, C) qRT-PCR analysis of pluripotency markers at the DE stage and hepatic endoderm markers at the HE stage following each indicated protocol. The data represent means±s.d., n=12. (D) The microscopic morphology of mature hepatocyte-like cells from different protocols. (E) qRT-PCR analysis of hepatocyte markers at the iPSC-MH stage. The data represent means±s.d., n=6. (F) Reproducible generation of iPSC-MH from multiple donor-derived iPSC clones. The data are shown as ng/ml/24 hour/ $2\times10^5$ cells. n=10. (G) ELISA quantification of secreted cerberusl (DE marker) during the day 4 to day 10 transition.

FIG. 9 (Figure S5) Optimization of iPSC-derived liver bud generation protocols. (A) Liver buds from iPSCs (day 0), DE (day 6 or 7), HE (day 10) and MH (day 14) cells. Gene expression analyses revealed that only the day 6 and day 10 endodermal cells exhibited the highest hepatic functions after extended culture. (B) Hierarchical clustering of 2-D cells: iPSC, DE, HE, IH and MH; and 3-D tissues: human iPSC-liver buds, human fetal and adult liver tissues using signatures developed by Si-Tayeb et al. (Si-Tayeb et al., 2010). FLT, 10 gwk or 22-40 gwk pool Fetal Liver Tissue; ILT, 0 yr Infant Liver Tissue; ALT, 5 yrs, 30 yrs, 44 yrs or 55 yrs old Liver Tissues; AHEP, human primary hepatocytes; AHEP-3D, 3D cultured human primary hepatocytes. (C) The GSEA analysis and heatmap visualization of angiogenesis hallmark genes between day 6 and day 8 buds.

FIG. 10 (Figure S6) Identification of TBX3 and ADRA1B as markers of iPSC-tHEs. (A, B) Time-dependent expression of TBX3 in panel A and ADRA1B in panel B. The data represent means±s.d., n=3.

FIG. 11 (Figure S7) Highly efficient differentiation into primitive endothelial progenitors from feeder free human iPSCs.
(A) Four independent step-wise specification protocols for EC differentiation. (B) Microscopic characterization of iPSC-ECs which underwent respective differentiation, followed by FACS-based initial screen with CD31 and CD144. (C) qRT-PCR-based analysis of the EC markers. (D) Growth curve of iPSC-EC after four times of passaging.

FIG. 12 (Figure S8) In vivo functionalization of human iPSC liver buds.
(A) Whisker plot comparison (5-95 percentile) of ALB levels in all iPSC-LB transplanted group at day 40. Each graph represents raw value collected from all 10 different mice. (B) Time-dependent human serum albumin production in the presence or absence of iPSC-ECs and STM. The data represent means±s.e.m., n=6. *: P=0.0356. Transplanted cell number was $3\times10^6$ cell-equivalent LBs in panel A and panel B.

FIG. 13 In the directed differentiation from iPSC to DE, Wnt3a is replaceable with CHIR99021. FIG. 13A: Schematic diagram of a protocol using CHIR99021 as an alternative for Wnt3a. Upon studying various conditions, a condition was selected in which CHIR99021 (2 μM) is added for 3 out of the 6 days of DE directed differentiation. FIG. 13B: Cellular morphologies at respective differentiation stages of a conventional method using Wnt3a and under the condition where CHIR99021 (2 μM) is added for 3 days. No morphological changes are observed compared to the case of using Wnt3a. FIG. 13C: Analysis of positive ratios for CXCR4 (a DE marker) by flow cytometry at the DE stage of the conventional method using Wnt3a and under the condition where CHIR99021 (2 μM) is added for 3 days. The positive ratio for CXCR4 when CHIR99021 is added is comparable to the case of using Wnt3a. FIG. 13D: Expression analysis of various differentiation markers by quantitative PCR (qPCR). The results were comparable to the case of using Wnt3a. FIG. 13E: ELISA analysis of albumin secretion at the MH stage. In multiple iPSC clones with CHIR99021, albumin secretion was comparable to, or even higher than, that of the case using Wnt3a.

Figure 14:
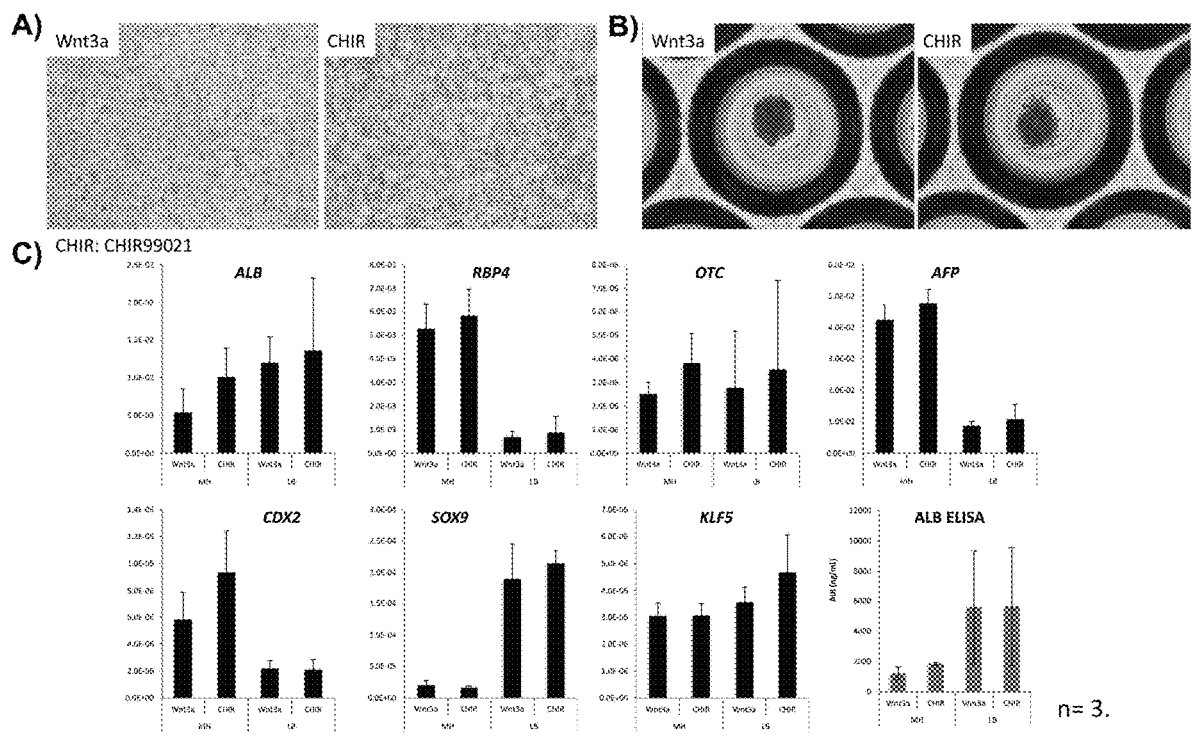

FIG. 14 Comparison of Wnt3a and CHIR99021 (in vitro MH, LB) FIG. 14A and B: Cellular morphologies in MH (FIG. 14A) and LB (FIG. 14B). No morphological differences are observed compared to the case of using Wnt3a. FIG. 14C: Marker expression analyses in MH and LB by qPCR. Expressions with CHIR99021 are c to those of the case using Wnt3a; there is observed no increase in the expression of marker genes belonging to other cell lineages (such as intestinal markers).

Figure 15:
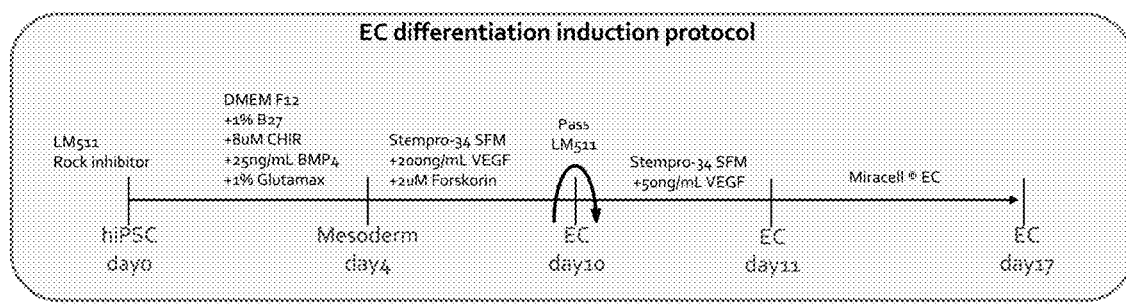

FIG. 15 EC induction. A revised protocol for directed differentiation to iPSC-derived vascular endothelial cell (iPSC-EC).

Figure 16:
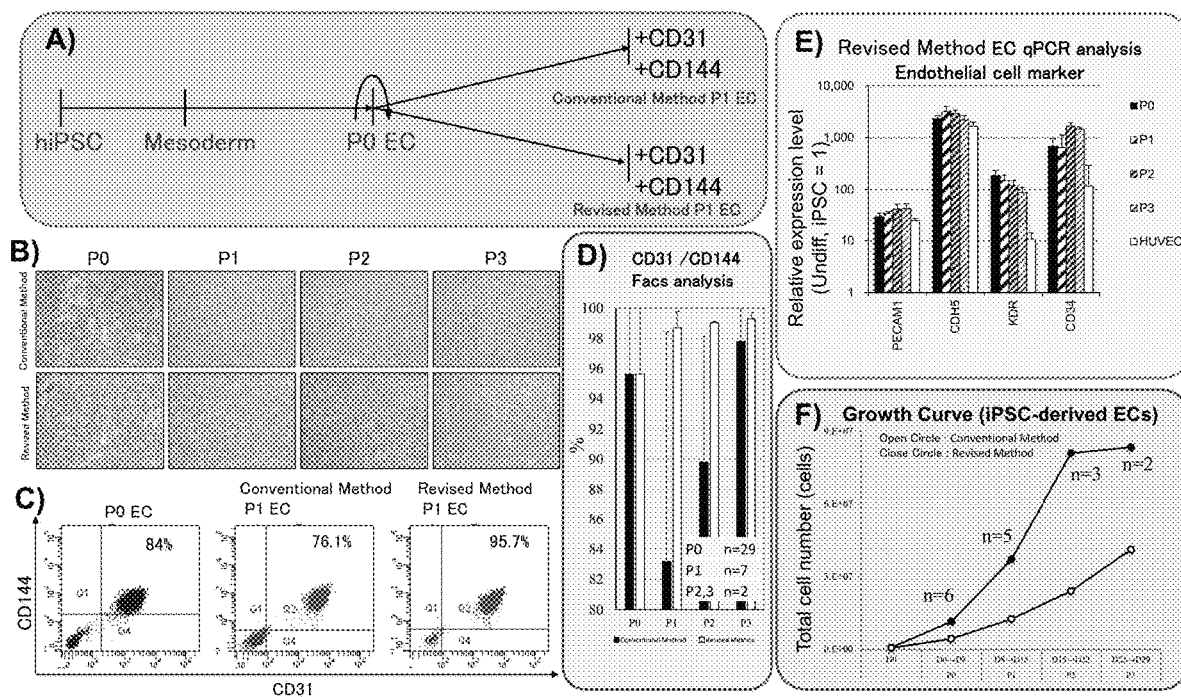

FIG. 16 Study of directed differentiation medium intended for clinical application. FIG. 16A: A schematic diagram of directed differentiation protocol. FIG. 16B: Cellular morphologies in the conventional method and the revised method. No morphological differences are observed. FIG. 16C: Analysis by flow cytometry of positive ratios for EC marker in the conventional method and the revised method. FIG. 16D: A summary of the flow cytometry analysis in FIG. 16C. High positive ratios for CD31/CD144 are obtained more stably in the revised method than in the conventional method. FIG. 16E: Expression analyses of individual differentiation markers by qPCR. Expressions of EC markers are stable in the revised method even after passages. FIG. 16F: Cell growth upon each passage. Growth capacity after passages is high in the revised method compared to the conventional method.

BEST MODES FOR CARRYING OUT THE INVENTION

Hereinbelow, the present invention will be described in detail. The present invention provides an organ bud prepared from vascular cells, mesenchymal cells and tissue or organ cells, wherein each of the vascular cell, the mesenchymal cell and the tissue or organ cell has been induced from pluripotent stem cells.

In the present invention, the term "organ bud" means a structure capable of differentiating into an organ through maturing, the structure comprising three types of cells which are vascular cells, mesenchymal cells and tissue or organ cells. Whether a structure is an organ bud or not can be judged, for example, by transplanting the structure into an organism and examining whether or not it is capable of differentiating into an organ of interest (the structure can be judged as organ bud if it has differentiated into the organ of interest); and/or by examining whether or not the structure comprises all of the above-described three types of cells (the structure can be judged as organ bud if it comprises all of the three types of cells). The organ bud may be one which differentiates into an ectodermal organ such as brain, spinal cord, adrenal medulla, epidermis, hair/nail/dermal gland, sensory organ, peripheral nerve or lens; a mesodermal organ such as spleen, kidney, urinary duct, heart, blood, gonad, adrenal cortex, muscle, skeleton, dermis, connective tissue or mesothelium; or an endodermal organ such as liver, pancreas, digestive tract (pharynx, esophagus, stomach, intestinal tract), lung, thyroid, parathyroid, urinary tract or thymus. Preferably, the organ bud is one which differentiates into an endodermal organ; e.g., one which differentiates into liver (liver bud), one which differentiates into pancreas (pancreas bud), or one which differentiates into intestinal tract. Whether an organ bud is one which differentiates into an endodermal organ or not can be judged by examining the expression of marker proteins (if any one or a plurality of the marker proteins described later are expressed, the organ bud can be judged as the organ bud of interest). For example, HHEX, SOX2, HNF4A, AFP, ALB and the like are markers for liver buds; PDX1, SOX17, SOX9 and the like are markers for pancreas bud; and CDX2, SOX9 and the like are markers for organ buds which differentiate into intestinal tract. Among the terms used by those skilled in the art, the following are included in the organ bud of the present invention: liver bud, liver diverticula, liver organoid, pancreatic (dorsal or ventral) buds, pancreatic diverticula, pancreatic organoid, intestinal bud, intestinal diverticula, intestinal organoid (K. Matsumoto, et al. Science. 19; 294 (5542): 559-63 (2001)) and so on.

The organ bud of the present invention is prepared from vascular cells, mesenchymal cells and tissue or organ cells, all of these three types of cells being entirely derived from pluripotent stem cells.

As pluripotent cells, the following may be enumerated, for example: pluripotent cells obtained from organisms [e.g., ES cells, pluripotent cells induced by reprogramming such as iPS cells, MUSE cells (Multilineage-differentiating stress-enduring (Muse) cells are a primary source of induced pluripotent stem cells in human fibroblasts. PNAS, 2011), iMPC cells (induced multipotent progenitor cell; Mouse liver repopulation with hepatocytes generated from human fibroblasts. Nature, 2014)] and a combination thereof.

Pluripotent stem cells may be human-derived. Alternatively, pluripotent cells may also be derived from non-human animals (e.g., animals used as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab and the like).

The organ bud of the present invention may be prepared by co-culturing in vitro three types of cells (vascular cells, mesenchymal cells and tissue or organ cells) induced from pluripotent stem cells. The present invention provides a method of preparing an organ bud, comprising culturing vascular cells, mesenchymal cells and tissue or organ cells in vitro, wherein each of the vascular cell, the mesenchymal cell and the tissue or organ cell has been induced from pluripotent stem cells.

In the present invention, the term "tissue or organ cell" is a concept encompassing cells differentiated into functional cells constituting tissues or organs, or undifferentiated cells which are capable of differentiating into such functional cells. Undifferentiated cells include stem cells, progenitor cells, endoderm cells, organ bud cells, and so on. Preferably, undifferentiated cells are those cells which are destined to, but are yet to, differentiate into functional cells. Examples of "undifferentiated tissue or organ cell" include, but are not limited to, cells capable of differentiating into an organ such as kidney, heart, lung, spleen, esophagus, stomach, thyroid, parathyroid, thymus, gonad, brain or spinal cord; cells capable of differentiating into an ectodermal organ such as brain, spinal cord, adrenal medulla, epidermis, hair/nail/dermal gland, sensory organ, peripheral nerve or lens; cells capable of differentiating into a mesodermal organ such as spleen, kidney, urinary duct, heart, blood, gonad, adrenal cortex, muscle, skeleton, dermis, connective tissue or mesothelium; and cells capable of differentiating into an endodermal organ such as liver, pancreas, digestive tract (pharynx, esophagus, stomach, intestinal tract), lung, thyroid, parathyroid, urinary tract or thymus. Whether or not a certain cell is capable of differentiating into an ectodermal organ, mesodermal organ or endodermal organ can be determined by checking for the expression of marker proteins (if any one or more of marker proteins are expressed, the cell can be judged as a cell capable of differentiating into an ectodermal organ, mesodermal organ or endodermal organ). For example, in cells capable of differentiating into liver, HHEX, SOX2, HNF4A, AFP, ALB and the like are markers; in cells capable of differentiating into pancreas, PDX1, SOX17, SOX9 and the like are markers; in cells capable of differentiating into intestinal tract, CDX2, SOX9 and the like are markers; in cells capable of differentiating into kidney, SIX2 and SALL1 are markers; in cells capable of differentiating into heart, NKX2-5, MYH6, ACTN2, MYL7 and HPPA are markers; in cells capable of differentiating into blood, C-KIT, SCA1, TER119 and HOXB4 are markers; and in cells capable of differentiating into brain or spinal cord, HNK1, AP2, NESTIN and the like are markers. Among the terms used by those skilled in the art, the following are included in the "undifferentiated tissue or organ cell" of the present invention: hepatoblast, hepatic progenitor cells, hepatic precursor cells, pancreatoblast, pancreatic progenitors, pancreatic progenitor cells, pancreatic precursor cells, endocrine precursors, intestinal progenitor cells, intestinal precursor cells, intermediate mesoderm, metanephric mesenchymal precursor cells, multipotent nephron progenitor, renal progenitor cells, cardiac mesoderm, cardiovascular progenitor cells, cardiac progenitor cells (J R. Spence, et al. Nature.; 470(7332):105-9.(2011); Self, et al. EMBO J.; 25(21): 5214-5228. (2006); J. Zhang, et al. Circulation Research.; 104: e30-e41(2009); G. Lee, et al. Nature Biotechnology 25, 1468-1475 (2007)) and so on. Undifferentiated cells may be prepared from pluripotent stem cells such as induced pluripotent stem cells (iPS cells) or embryonic stem cells (ES cells) by known methods. For example, cells capable of differentiating into liver may be prepared as previously described (K.Si-Taiyeb, et al. Hepatology, 51 (1): 297- 305(2010); T. Touboul, et al. Hepatology. 51 (5):1754-65 (2010)); cells capable of differentiating into pancreas may be prepared as previously described (D. Zhang, et al. Cell Res.; 19(4):429-38 (2009)); cells capable of differentiating into intestinal tract may be prepared as previously described (J. Cai, et al. J Mol Cell Biol.; 2(1): 50-60 (2010); R. Spence, et al. Nature.; 470 (7332):105-9 (2011)); cells capable of differentiating into heart may be prepared as previously described (J. Zhang, et al. Circulation Research.; 104: e30-e41(2009); and cells capable of differentiating into brain or spinal cord may be prepared as previously described (G. Lee, et al. Nature Biotechnology 25, 1468-1475 (2007)). Examples of functional cells constituting organs or tissues include, but are not limited to, endocrine cells of pancreas, pancreatic duct epithelial cells of pancreas, hepatocytes of liver, epithelial cells of intestinal tract, tubular epithelial cells of kidney, podocytes of kidney, cardiomyocytes of heart, lymphocytes and granulocytes of blood, erythrocytes, neurons and glial cells of brain, and neurons and Schwann cells of spinal cord.

In the preparation of the organ bud of the present invention, tissue or organ cells prepared (induced by directed differentiation) from pluripotent stem cells are used.

With respect to directed differentiation from pluripotent stem cells (e.g., iPS cells) into hepatic endoderm cells (iPSC-HE), hepatic function has been greatly improved by using day 7 TBX3 and ADR1AB co-positive cells based on comparison of differentiation stages (see Example described later).

In the present specification, expressions such as "positive" or "+" used with respect to cell surface markers refer to a state in which expression of the relevant cell surface marker on the cell can be confirmed by immunostaining or the like. On the other hand, expressions such as "negative" or "−" refer to a state in which expression of the relevant marker cannot be confirmed by immunostaining or the like.

TBX3 and ADR1AB co-positive hepatic endoderm cells (iPSC-HE) may be prepared according to the method described in Example provided later (Protocols 1 to 3 of FIG. 8A, and FIG. 13A).

According to Protocol 1 of FIG. 8A, pluripotent stem cells may be cultured in the presence of a ROCK inhibitor, a factor belonging to the transforming growth factor β family, a factor belonging to the Wnt family and a class I histone deacetylase (HDAC) inhibitor (which may not be added) (e.g., for 1 to 2 days) and then cultured in the presence of a factor belonging to the transforming growth factor β family, a factor belonging to the Wnt family and a class I histone deacetylase (HDAC) inhibitor (which may not be added) (e.g., for 1 to 2 days). Subsequently, cells obtained through a step of further culturing in the presence of a factor belonging to the transforming growth factor 13 family and a factor belonging to the Wnt family (e.g., for 0 to 3 days) (definitive endoderm) are cultured in the presence of an FGF and a factor belonging to the TGF-β superfamily (e.g., for 1 to 4 days) for directed differentiation into TBX3 and ADR1AB co-positive cells.

According to Protocol 2 of FIG. 8A, pluripotent stem cells may be cultured in the presence of a ROCK inhibitor (e.g., for 1 to 2 days) and then cultured in the presence of a β catenin activator, a PI3K inhibitor and a factor belonging to the transforming growth factor β family (e.g., for 1 to 2 days). Subsequently, cells obtained through a step of further culturing in the presence of a factor belonging to the transforming growth factor β family and a BMP inhibitor (e.g., for 2 to 4 days) (definitive endoderm) are cultured in the presence of an FGF and a factor belonging to the TGF-β superfamily (e.g., for 1 to 4 days) for directed differentiation into TBX3 and ADR1AB co-positive cells.

According to Protocol 3 of FIG. 8A, pluripotent stem cells may be cultured in the presence of a ROCK inhibitor (e.g., for 1 to 2 days) and then cultured in the presence of a factor belonging to the transforming growth factor β family (e.g., for 2 to 5 days). Cells obtained through the above step (definitive endoderm) are cultured in the presence of an FGF and a factor belonging to the TGF-β superfamily (e.g., for 1 to 4 days) for directed differentiation into TBX3 and ADR1AB co-positive cells.

According to the protocol of FIG. 13A, pluripotent stem cells may be cultured in the presence of a ROCK inhibitor, a factor belonging to the transforming growth factor β family, a β catenin activator and a class I histone deacetylase (HDAC) inhibitor (which may not be added) (e.g., for 1 to 2 days) and then cultured in the presence of a factor belonging to the transforming growth factor β family, a β catenin activator and a class I histone deacetylase (HDAC) inhibitor (which may not be added) (e.g., for 1 to 2 days). Subsequently, cells obtained through a step of further culturing in the presence of a factor belonging to the transforming growth factor β family (e.g., for 0 to 4 days) (definitive endoderm) are cultured in the presence of an FGF and a factor belonging to the TGF-β superfamily (e.g., for 1 to 4 days) for directed differentiation into TBX3 and ADR1AB co-positive cells.

An additional culture step may be included before or after each of the above-described culture steps of directed differentiation from pluripotent stem cells into TBX3 and ADR1AB co-positive cells.

In the present invention, the term "vascular cell" is a concept encompassing cells differentiated into blood-constituting cells or undifferentiated cells which are capable of differentiating into such cells. Undifferentiated cells include stem cells, progenitor cells, mesodermal cells, and the like. Preferably, undifferentiated cells are those cells which are destined to, but are yet to, differentiate into vascular cells. Examples of vascular cells include, but are not limited to, vascular endothelial cells, vascular endothelial progenitor cells, endocardial progenitor cells and angioblasts. Among them, vascular endothelial cells are preferable. Whether or not a certain cell is a vascular endothelial cell can be determined by checking for the expression of marker proteins such as TIE2, VEGFR-1, VEGFR-2, VEGFR-3 or CD41 (if any one or more of the above marker proteins are expressed, the cell can be judged as a vascular endothelial cell). Vascular endothelial cells used in the present invention may be either differentiated or undifferentiated. Whether or not a certain vascular endothelial cell is differentiated can be determined with CD31 and CD144. Among the terms used by those skilled in the art, the following are included in the vascular endothelial cell of the present invention: endothelial cells, umbilical vein endothelial cells, endothelial progenitor cells, endothelial precursor cells, vasculogenic progenitors, hemangioblast (H J. joo, et al. Blood. 25; 118(8): 2094-104 (2001)) and so on.

In the preparation of the organ bud of the present invention, vascular cells prepared (induced by direct differentiation) from pluripotent stem cells are used.

Directed differentiation from pluripotent stem cells (e.g., iPS cells) into vascular endothelial cells (iPSC-EC) may be performed as follows. Briefly, pluripotent stem cells are dissociated and seeded in the presence of Rho kinase, and then cultured in Medium 1 (DMEM/F12 medium supplemented with 1-2% B27, 1% Glutamax, 25 ng/mL BMP4 and 8 μM CHIR 99021) for 3 days and in Medium 2 (StemPro34-SFM supplemented with 200 ng/mL VEGF and 2 μM Forskolin) for 3 to 4 days. Alternatively, culture may be performed in Medium 3 (StemPro34-SFM supplemented with 50 ng/mL VEGF) for up to 7 days. The thus prepared vascular endothelial cells (iPSC-EC) are subjected to immunostaining or FACS for examining the expression of a vascular endothelial marker CD31 (PECAM1). They are suitable for use in the present invention if 90% or more of them are found to express CD31. Gene expression analyses revealed high-yield expression of vascular endothelial markers PECAM1, CDH5, KDR, CD34, etc., with a 10- to more than 100-fold increase as compared to their expressions in iPS cells before directed differentiation (see Example described later). In addition to the expression of vascular endothelial marker CD31, expressions of CD144 and CD309 proteins can be confirmed by immunostaining (see Example described later).

The present invention provides a method of preparing CD31 and CD144 co-positive cells, comprising culturing pluripotent stem cells in the presence of a ROCK inhibitor, a β catenin activator and a factor belonging to the TGF-β superfamily (e.g., for 1 to 2 days), then culturing the cells in the presence of a β catenin activator and a factor belonging to the TGF-β superfamily (e.g., for 2 to 3 days), and further culturing the cells in the presence of a vascular endothelial growth factor receptor (VEGFR) agonist and an adenylate cyclase activator (e.g., for 4 to 8 days) (Pr1 of FIG. 11A). The CD31 and CD144 co-positive cells may be iPSC-EC. The CD31 and CD144 co-positive cells may be used in the preparation of organ buds.

The present invention also provides a method of preparing CD31 and CD144 co-positive cells, comprising culturing pluripotent stem cells in the presence of a ROCK inhibitor, a VEGFR agonist, a factor belonging to the transforming growth factor β family, a β catenin activator and a factor belonging to the TGF-β superfamily (e.g., for 1 to 2 days), then culturing the cells in the presence of a VEGFR agonist, a factor belonging to the transforming growth factor β family, a β catenin activator and a factor belonging to the TGF-β superfamily (e.g., for 2 to 4 days) and further culturing the cells in the presence of a VEGFR agonist and an inhibitor of TGF-β type I receptor (e.g., for 4 to 7 days) (Pr2 of FIG. 11A). The CD31 and CD144 co-positive cells may be iPSC-EC. The CD31 and CD144 co-positive cells may be used in the preparation of organ buds.

The present invention also provides a method of preparing CD31 and CD144 co-positive cells, comprising culturing pluripotent stem cells in the presence of a ROCK inhibitor and a factor belonging to the transforming growth factor 13 family (e.g., for 1 to 2 days), then culturing the cells in the presence of a factor belonging to the transforming growth factor β family (e.g., for 1 to 3 days), further culturing the cells in the presence of an FGF and a factor belonging to the TGF-β superfamily (e.g., for 1 to 3 days), and subsequently culturing the cells in the presence of a VEGFR agonist (e.g., for 2 to 7 days) (Pr3 of FIG. 11A). The CD31 and CD144 co-positive cells may be iPSC-EC. The CD31 and CD144 co-positive cells may be used in the preparation of organ buds.

The present invention also provides a method of preparing CD31 and CD144 co-positive cells, comprising culturing pluripotent stem cells in the presence of a ROCK inhibitor and a factor belonging to the TGF-β superfamily (e.g., for 1 to 2 days), then culturing the cells in the presence of a factor belonging to the TGF-β superfamily (e.g., for 2 to 4 days), and further culturing the cells in the presence of a factor belonging to the TGF-β superfamily, a VEGFR agonist and an FGF (e.g., for 2 to 7 days) (Pr4 of FIG. 11A). The CD31 and CD144 co-positive cells may be iPSC-EC. The CD31 and CD144 co-positive cells may be used in the preparation of organ buds.

An additional culture step may be included before or after each of the above-described culture steps of directed differentiation from pluripotent stem cells into CD31 and CD144 co-positive cells.

Further, it is also possible to raise the positive ratio(s) for CD31 and/or CD144 by re-seeding the CD31 and CD144 co-positive cells and culturing them in an extension medium (Example 3 described later). The extension medium may be exchanged with one of a different type after lapse of a specific time period. As the extension medium to be used at the time of re-seeding, StemPro-34SFM supplemented with VEGF-A is preferable. As a medium with which this medium is to be exchanged, Miracell™ EC (Takara Bio) is preferable. However, extension medium is not limited to these media. Preferably, a ROCK inhibitor is added for 1 day at the time of re-seeding.

In the preparation of the organ bud of the present invention, vascular cells are preferably CD31 and CD144 co-positive. Further, the vascular cells are preferably such that at least one gene selected from the group consisting of PECAM1, CDH5, KDR and CD34 is expressed in a higher yield than in pluripotent stem cells that are yet to undergo directed differentiation.

In the present invention, the term "mesenchymal cell" is a concept that encompasses cells differentiated into connective tissue cells that are mainly located in mesoderm-derived connective tissues and which form support structures for cells that function in tissues or undifferentiated cells which are capable of differentiating into such cells. Examples of the undifferentiated cell include, but are not limited to, stem cells, progenitor cells and mesodermal cells. Undifferentiated cells are preferably those cells which are destined to, but are yet to, differentiate into mesenchymal cells. Whether a certain cell is an undifferentiated mesenchymal cell or not may be determined by checking for the expression of marker proteins such as Stro-1, CD29, CD44, CD73, CD90, CD105, CD133, CD271 or Nestin (if any one or more of the above-listed marker proteins are expressed, the cell can be judged as undifferentiated mesenchymal cell). A mesenchymal cell in which none of the above-listed markers are expressed can be judged as a differentiated mesenchymal cell. Among the terms used by those skilled in the art, the following are included in the mesenchymal cell of the present invention: Septum Mesenchyme, Septum Transversum Mesenchyme, mesenchymal stem cells, mesenchymal progenitor cells, mesenchymal cells (R. Peters, et al. PLoS One. 30; 5(12):e15689 (2010)) and so on.

In the preparation of the organ bud of the present invention, mesenchymal cells prepared (induced by directed differentiation) from pluripotent stem cells are used.

Directed differentiation of pluripotent stem cells (e.g., iPS cells) into mesenchymal cells (iPSC-MC) may be performed as follows. Briefly, pluripotent stem cells are dissociated and seeded in the presence of Rho kinase, and then cultured in Medium 1 (DMEM/F12 medium supplemented with 1-2% B27, 1% Glutamax, 8 μM CHIR 99021 and 25 ng/mL BMP4) for 3 days and in Medium 2 (DMEM/F12 medium supplemented with 1-2% B27, 1% Glutamax, 10 ng/ml PDGFBB and 2 ng/ml Activin A) for 2 days. The cells cultured further in Medium 3 (DMEM/F12 medium supplemented with 1-2% B27, 1% Glutamax, 10 ng/ml bFGF and 12 ng/mL BMP4) for 2 days may be used. Alternatively, the resultant cells may further be subjected to maintenance culture in a medium for mesenchymal cells (such as MSCGM). The thus prepared mesenchymal cell (iPSC-MC) may be a cell that is CD166 positive and which does not express a vascular endothelial marker CD31 (PECAM1).

The present invention also provides a method of preparing CD166 positive but CD31 negative cells, comprising culturing pluripotent stem cells in the presence of a ROCK inhibitor, a β catenin activator and a factor belonging to the TGF-β superfamily (e.g., for 1 to 2 days), then culturing the cells in the presence of a β catenin activator and a factor belonging to the TGF-β superfamily (e.g., for 3 to 5 days), culturing the cells in the presence of a PDGF receptor agonist and a factor belonging to the transforming growth factor β family (e.g., for 1 to 4 days), further culturing in the presence of an FGF and a factor belonging to the transforming growth factor β family (e.g., for 2 to 6 days), and subjecting the resultant cells to maintenance culture in a medium for mesenchymal cells (e.g., for 3 to 20 days). An additional culture step may be included before or after each of the above-described culture steps of directed differentiation from pluripotent stem cells into CD166 positive but CD31 negative cells. The CD166 positive but CD31 negative cells may be mesenchymal cells (iPSC-MC). The CD166 positive but CD31 negative cells may be used in the preparation of organ buds.

Specific examples of medium for mesenchymal cells include, but are not limited to, MSCGM.

In the preparation of the organ bud of the present invention, mesenchymal cells may be septum transversum mesenchyme (STM) cells. STM cells may be LHX2 and WT1 co-positive. Transcription of FOXF1, HLX1, COL4A and ALCAM is activated in STM cells, and the cells may be LHX2 positive, WT1 positive and MIIA positive.

The present invention also provides a method of preparing LHX2 and WT1 co-positive cells, comprising culturing pluripotent stem cells in the presence of a ROCK inhibitor, a β catenin activator and a factor belonging to the TGF-β superfamily (e.g., for 1 to 2 days), then culturing the cells in the presence of a β catenin activator and a factor belonging to the TGF-β superfamily (e.g., for 3 to 5 days), further culturing the cells in the presence of a PDGF receptor agonist and a factor belonging to the transforming growth factor β family (e.g., 1 to 4 days), and culturing the cells in the presence of an FGF and a factor belonging to the transforming growth factor β family (e.g., for 2 to 6 days). An additional culture step may be included before or after each of the above-described culture steps of directed differentiation from pluripotent stem cells into LHX2 and WT1 co-positive cells. The LHX2 and WT1 co-positive cells may be septum transversum mesenchyme (STM) cells. The LHX2 and WT1 co-positive cells may be used in the preparation of organ buds.

Hereinbelow, factors which may be used in the above-described method of directed differentiation from pluripotent stem cells into three types of cells (organ cells, vascular cells and mesenchymal cells) will be described.

As ROCK inhibitors, Y-27632, GSK429286A, SR3677, Ripasudil (K-115), Fasudil, Thiazovivin or the like may be enumerated. Among them, Y-27632 is preferable.

As factors belonging to the transforming growth factor β family, Activin A, Nodal or the like may be enumerated. Among them, Activin A is preferable.

As factors belonging to the Wnt family, Wnt3a, Wnt3a-AFM, CHIR99021, R-Spondin-1, BIO (6-bromoindirubin-3'-oxime) or the like may be enumerated. Among them, Wnt3a is preferable. The factor belonging to the Wnt family may be one which is capable of activating β catenin.

As class I histone deacetylase (HDAC) inhibitors, butyrates (such as sodium butyrate), Valproic Acid, Panobinosta (LBH589), Apicidin, BML-210, Depudecin, HC Toxin, M344, Oxamflatin, Scriptaid, Splitomicin, Suberoyl bis-hydroxamic acid, Trichostatin A, Vorinostat (SAHA, MK0683), Entinostat (MS-275), Panobinostat (LBH589), Mocetinostat (MGCD0103), Biphenyl-4-sulfonyl chloride, ACY-738, Belinostat (PXD101), Romidepsin (FK228, Depsipeptide), MC1568, Tubastatin A, Givinostat (ITF2357), Dacinostat (LAQ824), CUDC-101, Quisinostat (JNJ-26481585), Pracinostat (SB939), PCI-34051, Droxinostat, Abexinostat (PCI-24781), RGFP966, AR-42, Rocilinostat (ACY-1215), Tacedinaline (CI994), CUDC-907, Curcumin, Tubacin, RG2833 (RGFP109), Resminostat, Divalproex Sodium, Sodium Phenylbutyrate, Tubastatin A, TMP269, Santacruzamate A (CAY10683), TMP195, Tasquinimod, BRD73954, Citarinostat (ACY-241), HPOB, LMK-235, Nexturastat A, Tucidinostat (Chidamide), (-)-Parthenolide, CAY10603, 4SC-202, BG45, ITSA-1 (ITSA1) or the like may be enumerated. Among them, sodium butyrate is preferable.

As FGF (fibroblast growth factor), basic FGF (also expressed as bFGF or FGF2), FGF4, FGFC (chimeric fibroblast growth factor) or the like may be enumerated. Among them, basic FGF is preferable.

As factors belonging to the TGF-β superfamily, BMP4, BMP2, BMP or the like may be enumerated. Among them, BMP4 is preferable.

As β catenin activators, CHIR99021, Wnt3a, Wnt3a-AFM, R-Spondin-1, BIO (6-bromoindirubin-3'-oxime) or the like may be enumerated. Among them, CHIR99021 is preferable. CHIR99021 can be an alternative for Wnt3a in the directed differentiation from iPSC into DE (Example 2 described later; CHIR d3 of FIG. 13A).

As PI3K inhibitors, PI-103, ZSTK474, NVP-BEZ235, LY294002, Wortmannin or the like may be enumerated. Among them, PI-103 is preferable. PI3K inhibitor may be PI3K, Akt and mTOR inhibitor.

As BMP inhibitors, LDN-193189, Galunisertib (LY2157299), LY2109761, SB525334, SB505124, Pirfenidone, GW788388, LY364947, RepSox, K02288, SD-208, LDN-214117, SIS3 HCl, Vactosertib (TEW-7197), DMH1, LDN-212854, ML347, Kartogenin, Hesperetin, Alantolactone or the like may be enumerated. Among them, LDN-193189 is preferable. BMP inhibitor may be an ALK2 and ALK3 inhibitor.

As vascular endothelial growth factor receptor (VEGFR) agonists, VEGF, VEGF-A, VEGF-B, VEGF-C, VEGF-D, VEGF-E, PlGF or the like may be enumerated. Among them, VEGF is preferable.

As adenylate cyclase activators, Forskolin, HJC0350, 8-Br-cAMP, Adenosine 3',5'-cyclic monophosphate (cAMP), Dibutyryl-cAMP (Bucladesine) or the like may be enumerated. Among them, Forskolin is preferable. Adenylate cyclase activator may be one that increases intracellular cAMP levels.

As inhibitors of TGF-β type I receptor, SB431542, LDN-193189, Galunisertib (LY2157299), LY2109761, SB525334, SB505124, GW788388, LY364947, RepSox, LDN-193189, K02288, LDN-214117, SD-208, Vactosertib (TEW-7197), ML347, LDN-212854, DMH1, Pirfenidone, Alantolactone, SIS3, Hesperetin or the like may be enumerated. Among them, SB431542 is preferable. Inhibitor of TGF-β type I receptor may be an ALK4, ALK5 and ALK7 inhibitor and an activin inhibitor as well.

As PDGF receptor agonists, PDGFBB, PDGF-AA, PDGF-AB, PDGF-CC, PDGF-DD or the like may be enumerated. Among them, PDGFBB is preferable.

Culture ratios of the three cell types in coculture are not particularly limited as long as the ratio enables the formation of organ buds. A preferable cell count ratio is as follows. Tissue or organ cell:vascular endothelial cell:mesenchymal cell=10:10-5:2-1.

The medium used for culturing is not particularly limited. Any medium may be used as long as it enables the formation of organ buds. Preferably, a medium for culturing vascular cells (e.g., vascular endothelial cells), a medium for culturing tissue or organ cells or a mixture of these two media may be used. As a medium for culturing vascular endothelial cells, any medium may be used but, preferably, a medium containing at least one of the following substances may be used: hEGF (recombinant human epidermal growth factor), VEGF (vascular endothelial growth factor), hydrocortisone, bFGF, ascorbic acid, IGF1, FBS, antibiotics (e.g., gentamycin or amphotericin B), heparin, L-glutamine, phenol red and BBE. Specific examples of this medium which may be used in the present invention include, but are not limited to, EGM-2 BulletKit (Lonza), EGM BulletKit (Lonza), VascuLife EnGS Comp Kit (LCT), Human Endothelial-SFM Basal Growth Medium (Invitrogen) and human microvascular endothelial cell growth medium (TOYOBO). As a medium for culturing tissue or organ cells, any medium may be used but, when the organ cell is hepatocyte, a medium containing at least one of the following substances may be preferably used: ascorbic acid, BSA-FAF, insulin, hydrocortisone and GA-1000. As a medium for culturing hepatocyte, HCM BulletKit (Lonza) from which hEGF (recombinant human epidermal growth factor) has been removed and RPMI1640 (Sigma-Aldrich) to which 1% B27 Supplements (GIBCO) and 10 ng/mL hHGF (Sigma-Aldrich) have been added may typically be used. With respect to formation of human liver buds, use of a medium prepared as described below has been found effective for maturation of liver buds. Briefly, GM BulletKit (Lonza) and HCM BulletKit (Lonza) from each of which hEGF has been removed are mixed at 1:1 and to the resultant mixture, dexamethasone, oncostatin M and HGF are added.

Although scaffold materials need not be used for culturing cells, a mixture of three types of cells may advantageously be cultured on a gel-like support that allows mesenchymal cells to contract.

Contraction of mesenchymal cells may be confirmed, for example, by noting the formation of a 3D tissue morphologically (either under microscope or with the naked eye) or by showing that the tissue is strong enough to retain its shape as it is collected with a spatula or the like (Takebe et al. Nature 499 (7459), 481-484, 2013).

The support may advantageously be a gel-like substrate having an appropriate stiffness [e.g., a Young's modulus of 200 kPa of less (in the case of a Matrigel-coated gel of a flat shape); however, the appropriate stiffness of the support may vary depending on the coating and shape]. Examples of such substrates include, but are not limited to, hydrogels (such as acrylamide gel, gelatin and Matrigel). The stiffness of the support need not be uniform and may vary with the shape, size and quantity of a cell condensate of interest so that it can be provided with a spatial/temporal gradient or can be patterned. In the case where the stiffness of the support is uniform, it is preferably 100 kPa or less, more preferably 1-50 kPa. The gel-like support may be planar, or alternatively, the side on which culture is to be performed may have a U- or V-shaped cross section. If the side of the gel-like support on which culture is to be performed has a U- or V-shaped cross section, cells tend to gather on the culture surface and a cell condensate can advantageously be formed from a smaller number of cells and/or tissues. Moreover, the support may be modified chemically or physically. Examples of modifying substances include, but are not limited to, Matrigel, laminin, entactin, collagen, fibronectin and vitronectin.

One example of the gel-like culture support that is provided with a spatial gradient of stiffness is a gel-like culture support that is stiffer in the central part than in the peripheral part. The stiffness of the central part is appropriately 200 kPa or less and it suffices that the peripheral part is softer than the central part. Appropriate values for the stiffness of the central and peripheral parts of the substrate are variable with the coating and the shape. Another example of the gel-like culture support that is provided with a spatial gradient of stiffness is a gel-like culture support that is stiffer in the peripheral part than in the central part.

One example of the patterned, gel-like culture support is a gel-like culture support having one or more patterns in which the central part is stiffer than the peripheral part. The stiffness of the central part is appropriately, 200 kPa or less and it suffices that the peripheral part is softer than the central part. Appropriate values for the stiffness of the central and peripheral parts of the substrate are variable with the coating and the shape. Another example of the patterned, gel-like culture support is a gel-like culture support having one or more patterns in which the peripheral part is stiffer than the central part. The stiffness of the peripheral part is appropriately 200 kPa or less and it suffices that the central part is softer than the peripheral part. Appropriate values for the stiffness of the central and peripheral parts of the substrate are variable with the coating and the shape.

The temperature during culture is not particularly limited but it is preferably 30-40° C. and more preferably 37° C.

The culture period is not particularly limited but it is preferably 3-10 days and more preferably 6 days.

In the present invention, the three types of cell species used for organ bud preparation are entirely derived from pluripotent stem cells, whereby the differentiation stages of the three types of cell species can be synchronized. By preparing organ buds from these cells, it is possible to improve the function of organ buds. Further, it becomes possible to reduce the costs and labor required for quality evaluation or production of the three types of cell species.

The organ bud of the present invention may be transplanted into a non-human animal, in which it is allowed to mature, whereby a tissue or organ can be prepared. Briefly, the present invention also provides a method of preparing a tissue or an organ, comprising transplanting the above-described organ bud into a non-human animal and differentiating the organ bud into a tissue or an organ. Examples of the non-human animal that may be used include animals that are used, for example, as experimental animals, pet animals, working animals, race horses or fighting dogs, more specifically, mouse, rat, rabbit, pig, dog, monkey, cattle, horse, sheep, chicken, shark, devilfish, ratfish, salmon, shrimp, crab and the like. Moreover, the non-human animal to be used herein is preferably an immunodeficient animal in order to avoid immunorejection.

Therefore, the present invention also provides a method of transplanting an organ bud, comprising transplanting the above-described organ bud into a human or a non-human animal. The site of transplantation of the organ bud may be any site as long as transplantation is possible. Specific examples of the transplantation site include, but are not limited to, the intracranial space, the mesentery, the liver, the spleen, the kidney, the kidney subcapsular space, and the supraportal space. For intracranial transplantation, about 1 to 3 organ buds of 5 mm in size, prepared in vitro, may be transplanted. For intramesenteric transplantation, about 1 to 6 organ buds of 5 mm in size, prepared in vitro, may be transplanted. For transplantation into the supraportal space, about 1 to 20 organ buds of 5 mm in size, prepared in vitro, may be transplanted. For transplantation into the kidney subcapsular space, about 1 to 5 organ buds of 5 mm in size, prepared in vitro, may be transplanted. For transplantation into the liver, spleen or kidney, about 100 to 200 organ buds of 100 pm in size, prepared in vitro, may be transplanted.

The thus prepared tissue or organ may be used in drug discovery screening or regenerative medicine.

Therefore, the present invention provides a method of regeneration or function recovery of a tissue or an organ, comprising transplanting the above-described organ bud into a human or a non-human animal and differentiating the organ bud into a tissue or an organ. As non-human animals, animals used for such purposes as experimental animal, pet animal, working animal, race horse or fighting dog, more specifically, mouse, rat, rabbit, pig, dog, monkey, cattle, horse, sheep, chicken, shark, devilfish, ratfish, salmon, shrimp, crab or the like may be used.

The organ bud of the present invention may be formulated and used in the form of a composition for regenerative medicine. This composition of the present invention may be transplanted into a living body to prepare a tissue or an organ. Regeneration or function recovery of a tissue or an organ is also possible by transplanting the composition of the present invention into a living body.

Upon transplantation of the composition of the present invention into a living body, the organ bud may differentiate into a tissue or an organ with vascular networks. In such vascular networks, blood perfusion may occur. It is believed that the occurrence of blood perfusion in vascular networks enables generation of a tissue or an organ with a highly ordered tissue structure equivalent or close to the tissue structure of adult tissues.

The composition of the present invention may comprise a tissue vascularization promoter such as FGF2, HGF or VEGF, a gelatin sponge for hemostasis to cope with the bleeding from transplantation (product name: Spongel; Astellas Pharma), and a tissue adhesive for fixing transplants such as Bolheal (Teijin Pharma), Beriplast™ (CSL Behring) or TachoComb™ (CSL Behring).

The present invention also provides a method of preparing a non-human chimeric animal, comprising transplanting the above-described organ bud into a non-human animal and differentiating the organ bud into a tissue or an organ. The non-human animal (e.g., mouse) transplanted with the organ bud may mimic the physiological function of the organismal species (e.g., human) from which the tissue or organ cell used for preparing the organ bud is derived.

Still further, the present invention provides a method of evaluating a drug, comprising using at least one member selected from the group consisting of the organ bud, the tissue or organ and the non-human chimeric animal as prepared by the above-described methods, respectively. Specific examples of drug evaluation include, but are not limited to, evaluation of drug metabolism (e.g., prediction of drug metabolism profiles), evaluation of drug efficacy (e.g., screening for drugs that are effective as pharmaceuticals), toxicity evaluation, and evaluation of drug interactions.

Evaluation of drug metabolism may be performed as follows. Briefly, at least one member selected from the group consisting of the organ bud, the tissue or organ and the non-human chimeric animal as prepared by the above-described methods, respectively, is administered with a candidate compound for pharmaceuticals and the resulting biological sample is then collected and analyzed, whereby a human-type drug metabolism profile can be obtained. As a result, prediction of the distribution/metabolism/excretion processes of pharmaceuticals in human (which was extremely difficult to achieve by conventional methods) becomes possible and it is expected that the development of safe and efficacious pharmaceuticals can be greatly accelerated.

Screening for drugs that are effective as pharmaceuticals may be performed as follows. Briefly, at least one member selected from the group consisting of the organ bud, the tissue or organ and the non-human chimeric animal as prepared from a cell established from a diseased patient by the above-described methods, respectively, is administered with a novel candidate compound for pharmaceuticals. This enables subsequent analysis. As a result, a potential is expected for achieving great improvement in the precision of drug efficacy prediction for the case of actual administration to human, which has been unsatisfactory in conventional in vitro tests.

Evaluation of toxicity may be performed as follows. Briefly, at least one member selected from the group consisting of the organ bud, the tissue or organ and the non-human chimeric animal as prepared by the above-described methods, respectively, is administered with a test substance and, thereafter, histological damage markers or the like are measured. This makes it possible to improve the precision of damage prediction.

Evaluation of drug interactions may be performed as follows. Briefly, at least one member selected from the group consisting of the organ bud, the tissue or organ and the non-human chimeric animal as prepared by the above-described methods, respectively, is administered with a plurality of drugs; then, each drug is examined for its pharmacokinetics such as distribution/metabolism/excretion processes, evaluated for its toxicity, and evaluated for its efficacy.

Further, it is also possible to create tissue stem cells from the tissue or organ prepared by the method of the present invention. Thus, the present invention is applicable to cell engineering techniques for large scale creation of human tissue cells and organ cells.

EXAMPLES

Hereinbelow, the present invention will be described in more detail with reference to the following Examples.

Example 1

Establishment of Massive Production Technique for Liver Buds from Human Pluripotent Stem Cells

SUMMARY

Organoid transplantation therapy may potentially become a revolutionary therapeutic paradigm but securing reproducibility and scalability has been a major challenge. In this study, the present inventors attempted to solve this problem by constructing a scalable production platform for organ buds entirely from human induced pluripotent stem cells (iPSC). First, by conducting massive "reverse" screen experiments, the present inventors identified three progenitor populations (hepatic endoderm, endothelium and septum transversum mesenchyme) that can effectively generate liver buds in a highly reproducible manner. Furthermore, the present inventors achieved the level of scalability required for transplantation therapy by developing an omni-well-array culture platform for mass producing homogeneous and miniaturized liver buds on a $>10^8$ scale. Liver tissues which were generated entirely from iPSCs, vascularized and yet functional significantly improved subsequent hepatic functionalization to be potentiated by interactions of progenitors at gradual developmental stages. Further, this liver tissue enabled functional rescue to be achieved for acute liver failure via transplantation. Overall, this study provides a manufacturing platform for supplying multicellular liver bud organoids, which is expected to greatly facilitate clinical and pharmaceutical applications for the treatment of liver diseases.

INTRODUCTION

"Organoid technology" is a recently evolving approach for the treatment of intractable diseases as well as human development and disease models (Huch and Koo, 2015, Lancaster and Knoblich, 2014, Sasai, 2013). Based on a self-condensation principle, the present inventors have recently succeeded in building an additional complexity into organoids by developing multicellular organ buds (such as liver bud, pancreatic bud, and kidney bud) with therapeutic potential in various mouse disease models (Takebe et al., 2013, Takebe et al., 2014, Takebe et al., 2015). Nevertheless, given the purpose of generating sufficiently large and stable organoids for transplantation and drug testing in humans, broader applications of organoid-based approaches are subject to scalability and reproducibility challenges (Ding and Cowan, 2013). To facilitate the future therapeutic application of organ-bud-based approaches, the present inventors aimed at establishing a comprehensive, scalable, and reproducible method for generating vascularized human liver buds (LBs) entirely from feeder-free human induced pluripotent stem cells (iPSCs) and validating their functional capacity for transplant application.

RESULTS

The present inventors first aimed at establishing a scalable three-dimensional (3D) organoid culture platform with liver bud (LB) as an example. The overall strategy is summarized in FIG. 1A and FIG. 1B. Briefly, the present inventors developed a U-bottom-shaped microwell plate by combinatorial chemistry techniques to develop a finely structured film by transfer of a mold structure accurately onto a resin. The microwell array of the present inventors has an extremely high aspect ratio (the aperture diameter of each dimple is ~500 µm and the depth is 400 µm, and the dimples were tightly and triangularly arranged at an interval of 30 µm, as shown in FIG. 1C). It is difficult to broadly transfer such an aspect ratio with a conventional molding machine. Therefore, the present inventors improved the transfer accuracy by employing an internally optimized molding machine (see Experimental Procedures). As a result, prototyping has proven to be successful with 24-well and 6-well formats (Elplasia RB [round bottom]; 600 spots per well in 24 wells and 3,000 spots per well in 6 wells). The present inventors then adapted these plates into LB culture by mixing the human-iPSC-derived hepatic endoderm (iPSC-HE), human umbilical cord vein endothelial cells (HUVECs), and bone marrow mesenchymal stem cells (BMSCs) as previously described (Takebe et al., 2013). Upon optimization of coating material (FIG. 5 (Fig. S1)), dimple shape (data not shown), mixture ratio (FIG. 6A-6C (Figure S2A-S2C)) and cell count (FIG. 6D-6F (Figure S2D-S2F)), miniaturized LBs can be effectively formed using the microwell-array-based approach (see Supplementary Text).

To intensively scale up this strategy, the present inventors have devised an omni (1: one)-well-array plate containing over 20,000 microspots per well (FIG. 7A (Figure S3A)). External dimensions of the frame (length, width, and height) of the omni-well-array plate meet the Society for Biomolecular Screening (SBS) standards as with common microplates. The plate was composed of two modules, a bottomless plate frame and a microwell transferred film, which were assembled by laser welding (FIG. 1A, left). The adaptation of microwell-transferred film used in 24-well/6-well formats was ineffective for the omni-well format, because the significant depression in the central portion led to abnormal organoid displacement and subsequent fusion (FIG. 1B (FIG. 1B), middle). Thus, the present inventors attempted to improve the flatness by (1) reducing the residual stress of the film and (2) enhancing the rigidity of the film. First, the present inventors minimized the molding pressure for transfer of patterns to lower the limit of mold transfer by optimizing the molding parameters, including mold temperature and pressing time, and by improving film deflection during laser welding. Second, the present inventors enhanced rigidity by thickening the film (FIG. 1B (FIG. 1B), caption). Among the various thickness conditions tested within a range of 0.8-1.4 mm, the present inventors found that 1.1 mm film thickness satisfied an acceptable rigidity without disturbing microscopic observation. The 3D profilometer demonstrated minimal height fluctuation under the improved conditions, enabling subsequent LB culture on a larger scale (FIG. 1B (FIG. 1B), right). Importantly, over 99% of the generated LBs were successfully collected by simple manual pipetting (FIG. 5B (Figure S1B)). Once the triple progenitors were seeded onto the omni-well plate, over 20,000 endothelialized LBs were self-organized, whereas LBs in single iPSC-HE culture were not self-organized (FIG. 1C, 1D (FIGS. 1C and 1D)). Quality verification analysis by qRT-PCR showed that LBs in the omni-well were comparable in property to those in 24-well/6-well formats (FIG. 7B (Figure S3B)). In conclusion, the present inventors successfully developed a prototypal design of an omni-well-array plate for massive organoid production.

Next, the present inventors attempted to define the phenotype of an optimal endoderm cell population for LB generation in humans. For this purpose, the present inventors performed massive "reverse" screen experiments by comparing the multiple endoderm stages based on the quality of resultant organoids. Following the selection of the most reproducible mature hepatocyte differentiation protocols previously described (FIG. 8A-F (FIGS. S4A-S4F; Supplemental Experimental Procedures) (Kajiwara et al., 2012, Loh et al., 2014, Si-Tayeb et al., 2010), the present inventors further attempted to precisely determine the best endoderm stages for iPSC-LB functionality by starting LB culture from day 0 to day 20 cells (FIG. 9 (Figures S5) and FIG. 2A and 2B (FIG. 2A and 2B)). First, fluorescence-based quantitative assessment of the morphologic variation of the collected LBs generated from multiple stages (days 0-20) revealed that day 8 cells were the only population capable of maintaining highly homogeneous LBs within 100-200 µm in size (FIG. 1E and 1F (FIGS. 1E and 1F). Subsequent qRT-PCR of hepatic marker genes (FIG. 9A (Figure S5A) and ELISA (FIG. 2A (FIG. 2A)) of protein production showed that day 8 cell-derived iPSC-LBs were higher in quality than day 0 (iPSC), 5, 6, 7, 10 and 20 cell-derived LB culture. Transcriptome analysis showed that the expression signatures of LBs were more similar to human adult liver tissues than 2D differentiated cells (FIG. 9 (Figure S5B)). Consistently, according to principal component analysis of overall gene expression, the PC1 axis demonstrated that the profiles of day 8 buds were closer to those of human adult liver tissue samples, compared to other stage buds (FIG. 2B (FIG. 2B)). Interestingly, a remarkable enrichment in angiogenesis hallmark gene set was observed in day 8 buds, but not in day 7 buds (FIG. 9C (Figure S5C)), which possibly contributes to favorable in vivo vascularization outcomes.

To further characterize this "reversely" identified day 8 population, the present inventors performed SOX17/HNF4A co-immunostaining-, qRT-PCR-, fluorescence-activated cell sorting (FACS)- and Cerberus1-ELISA-based profiling and identified that day 8 cells represent a transitional population from definitive endoderm to hepatic endoderm (HE) cells (FIG. 8G (Figure S4G) and FIG. 2C (FIG. 2C)). Herein, the day 8 cells are defined as transitional hepatic endoderm (tHE) cells. Although being negative for definitive endoderm (DE) makers, day 8 cells do not express an HE marker such as HNF4A (FIG. 2C (FIG. 2C)), so the present inventors attempted to define the cells by identifying definable markers by comparative transcriptome analysis between day 6 and day 8 populations. Volcano plot analysis (comparing iPSC-DE and iPSC-tHE) identified T-box transcription factor 3 (TBX3) and adrenoceptor alpha 1B (ADRA1B) based on transcriptome dynamics (FIG. 2D (FIGS. 2D) and FIG. 10 (Figure S6)), which was confirmed by immunostaining and qRT-PCR (FIG. 2E (FIG. 2E) and FIG. 3A (FIG. 3A)). Together although the developmental relevance of this reversely identified population remains elusive, the present inventors concluded that TBX3- and ADRA1B-co-positive tHE cells are the most effective stage for LB generation.

With respect to future applications of this LB-based approach, one major obstacle is the use of postnatal-tissue-derived stromal progenitors (i.e., HUVECs and BMSCs). Accordingly, the present inventors aimed at deriving two LB stromal progenitors from human iPSCs. During early liver organogenesis, HE cells migrate toward LIM homeobox 2 (LHX2)- and Wilms tumor 1 (WT1)-positive septum transversum mesenchyme (STM) to form LBs (Delgado et al., 2014, Kolterud et al., 2004). STM is involved not only in LB formation but also in the growth and survival of hepatoblasts mediated at least by STM-derived paracrine factors (Zaret, 2002). However, differentiation protocols for STM cells have not been developed (Iyer et al., 2015, Witty et al., 2014). In order to direct STM fate, the present inventors exposed potential inducers and their combinations in iPSC-derived lateral plate mesoderm (iPSC-Meso) at day 4. The transcriptional activation of the STM markers FOXF1, HNF4A, COL4A, and ALCAM was successfully induced by FGF2 and platelet-derived growth factor B (PDGFB) co-exposure at day 10, whereas the PSC marker NANOG and an early mesoderm marker T were barely detected (FIG. 2F (FIG. 2F)). Immunostaining of WT1, MIIA, and LHX2 also confirmed the correct cell fate induction in the presumptive STM cells (FIG. 3A (FIG. 3A)). Global gene array analysis suggested that iPSC-STM signatures show a remarkable shift toward reported human adult hepatic mesenchymal cell signatures (Asahina et al., 2009, Asahina et al., 2011, El Taghdouini et al., 2015) (FIG. 2G (FIG. 2G)). The present inventors previously demonstrated that one function of mesenchymal cells in LB generation is myosin-IIA-dependent self-condensation. Consistently, the present inventors demonstrated by time-lapse imaging that the self-condensation capacity of iPSC-STM was comparable to that of conventional BMSCs (FIG. 2H (FIG. 2H)).

In order to reproducibly generate endothelial progenitor cells (iPSC-EC), the present inventors developed four independent protocols that were modifications of previously described protocols, after adaptation into feeder-free iPSC culture (Narazaki et al., 2008, Orlova et al., 2014, Patsch et al., 2015, Samuel et al., 2013) (FIG. 11A (Figure S7A)). The iPSC-ECs subjected to full differentiation programs under each protocol were assessed by flow cytometric analysis (FACS) and qRT-PCR (FIG. 11B and 11C (Figures S7B and S7C)). The results revealed that cells following Protocol 1 exhibited the highest expression of endothelial cell (EC) markers, minimizing pluripotency markers. Even without purification by magnetic-bead-based sorting, the combination of VEGF and forskolin induced the highest levels of CD144 (VE-cadherin) and CD31 co-expression, as determined by periodical FACS analysis (>92.8%, n=12) (FIG. 21 (FIG. 20). After serial passaging, ECs rigorously proliferated (~200-fold increase) (FIG. 11D (Figure S7D)), and this expression was maintained up to 4 passages. This was confirmed by immunostaining of endothelial markers; cells exhibited rigorous migration and subsequent endothelial spouting potential upon plating on a Matrigel plug (FIG. 2J (FIG. 2J)). More importantly, co-cultivation of iPSC-EC and iPSC-STM on a soft substrate led to formation of condensed tissues (Takebe et al., 2015) and was capable of generating patent blood vessels 48 hr after transplantation, as confirmed by confocal imaging of cells by using AAVS1::mCherry iPSC-ECs after fluorescent dextran infusion (FIG. 2K (FIG. 2K)). These results suggested that human iPSC-STM and iPSC-EC populations are successfully differentiated from feeder-free iPSCs with functional capacity for self-condensation and vascularization.

The robust induction of triple progenitors enabled the present inventors to examine the potential for generation of LBs entirely from iPSCs (generation of "all iPSC-LB") (FIG. 3A (FIG. 3A)). These three distinct progenitors were successfully induced from multiple human feeder-free iPSC sources (5 independent donor-derived clones were tested), including HLA homozygous clones such as Ff-101 and Ff-114. 4D bright-field and light-sheet image analysis showed successful self-condensation in the presence of STM (FIG. 3B (FIG. 3B), top) and self-organizing iPSC-EC networks (FIG. 3B (FIG. 3B), bottom), respectively. Confocal wide-field imaging of 3-day-cultured tissues confirmed sprouted iPSC-ECs in alignment with iPSC-tHEs (FIG. 3C and 3D (FIGS. 3C and 3D)). Further, vascularization potential was assessed by transplantation into the cranial window of an immunodeficient mouse. Intravital imaging showed the formation of functional blood vessels at 48 hr and the eventual engraftment of iPSC-tHEs (FIG. 3E-3G (FIGS. 3E-3G)). iPSC-ECs directly anastomosed with mouse CD31 endothelial cells (FIG. 3H (FIG. 3H)) and were surrounded by iPSC-STMs at a perivascular location (FIG. 3I (FIG. 3I)). Thus, the present inventors have successfully generated vascularized and functional liver tissues entirely from human iPSCs.

Since transplantation of at least $10^8$ hepatocytes is required to correct a specific metabolic liver function (Martin et al., 2014), the ultimate challenge is to adapt the all-iPSC-LB strategy to a culture platform scalable up to omni-well-array scale. To this aim, our strategy for mass production and batch validation of all iPSC-LBs is outlined in FIG. 4A (FIG. 4A). Briefly, the present inventors prepared 5-10 omni-well-array plates for manufacturing $10^8$-cell-scale LBs per culture and characterized by in vitro functions and in vivo therapeutic potential. As a result, after 10 days of culture, mass-produced all iPSC-LBs not only exhibited higher albumin production (over 10 µg/mL/24 hr/$10^6$ cells) than conventional LBs (HUVEC/BMSC) or adult human hepatocytes (AdHep's) (FIG. 4B (FIG. 4B) and FIG. 9B (Figure S5B)) but also produced a number of key hepatic serum proteins, including complement factor H, coagulation factor VIII, transferrin, and AAT (FIG. 4C ((FIG. 4C)).

Remarkably, the ammonium clearance potential of long-term cultured all iPSC-LBs was comparable to that of primary AdHep's in culture (FIG. 4D (FIG. 4D)). Additional global transcriptome analysis indicated that differentiated all iPSC-LBs are more mature than conventional LBs, comparable to AdHep's, but less mature than 30-year-old human adult liver tissues (FIG. 4E (FIG. 4E) and FIG. 9B (Figure S5B)). In order to make a fair comparison with human AdHep's, the present inventors developed a scoring method based on their hepatic functional gene signature data. This method was designated APRES (aster plot of relative enrichment score) algorithm. Using hallmark gene sets in MSigDB version 5.0 (Subramanian et al., 2005), the present inventors determined the width of each component of the aster plot using the relative size of the modified normalized enrichment score (mNES) calculated from the expressional level of progressive signatures in human adult hepatocytes (AdHep 2D) over fetal liver (see Experimental Procedures). For each tissue or cell type, the relative mNES score was shown as the height of each component of the aster plot after multiplying width and the height of the component, and then the total relative score was defined as a summation. Unbiased APRES-based scoring clearly indicated that the profiles of differentiated all-iPSC-LBs were similar to those of AdHep and conventional iPSC-MH, including complement, angiogenesis, and cholesterol homeostasis cascades (FIG. 4F (FIG. 4F)).

Finally, functional batch validation of mass-produced human LBs was carried out in an immunodeficient mouse model of liver failure. $10^8$ hepatic cell-equivalent LBs were prepared and then $10^7$ cell-equivalent LBs were distributed among about 10 mice per mass production so as to evaluate the entire buds by assessing their therapeutic potential. Transplantation was performed into the renal subcapsular site of an Alb-Tk-NOG mouse. Overall, the results collected from 114 transplanted mice provided statistically significant robust evidence for survival improvement as achieved by rescuing total liver dysfunction (FIG. 4G (FIG. 4G)). Importantly, follow-up serum analysis also supported the fact that mass-produced LBs are functionally stable by increasing albumin (ALB) and decreasing alpha fetoprotein (AFP) (not detected) in vivo independent of the production cycle (FIG. 12A (Figure S8A)). Notably, the magnitude and persistence of human albumin were significantly higher than those obtained from human primary hepatocyte (n=12, 4 donors) transplantation (FIG. 4H (FIG. 4H)). The drug metabolism capacity of LBs was also confirmed by human-specific diclofenac metabolite detection (FIG. 4I (FIG. 4I)). Transplantation of stromal cell-free iPSC-tHE cells was barely functional, as assessed by human ALB in the transplant mice (FIG. 12B (Figure S8B)), suggesting the potential role of iPSC-STM and iPSC-EC in hepatic functionalization as was shown in a recent study of single-cell RNA sequencing (Camp et al., 2017). To summarize, the organoid mass-production culture platform of the present inventors not only addresses the scaling issue but also provides a stringent and reproducible differentiation platform for a human iPSC-derived liver tissue which is comparable in function to more than $10^8$ adult hepatocytes.

DISCUSSION

In conclusion, the technology outlined in this study sheds light on an exciting strategy for iPSC-based multicellular organoid supply for drug testing and regenerative applications. Especially, production of more than $10^8$-cell-scale LBs achieved in this Example seems a reasonable scale for human transplant applications, as numbers of hepatocyte transplantation trials have demonstrated clinical efficacy at a minimum dose of $10^8$ cells, especially for pediatric patients (Enosawa et al., 2014, Jorns et al., 2012). Given that the standard therapeutic scale is $10^9$ hepatocytes per patient or even more (Horslen and Fox, 2004), continued scaling efforts would be anticipated in a parallel efficacy study in animal models of metabolic disorders. Nevertheless, this protocol is being developed through multiple academic and industrial collaboration efforts with the use of clinical-grade components, including genetically characterized iPSCs, defined media and substrates, microwell-array plates, and microscopic verification as a preparation for future clinical trials. To accelerate this, complete adaptation of the all-iPSC-LB strategy into a current Good Manufacturing Practices (cGMP)-grade system will be critical for future clinical applications as well as for safety assessment through clinically relevant transplant routing. Ultimately, the present inventors believe that through the integration of an array of manufacturing technologies, it will be feasible to develop a clinically effective LB transplant therapy for treating currently intractable liver diseases.

Experimental Procedures

Human Liver Bud Culture in Microwells

All iPSC lines were maintained on dishes in StemFit™ (Ajinomoto); the dishes had been coated with Laminin 511™ E8 fragment (iMatrix-511, kindly provided by Nippi). Methods for directed differentiation into each lineage are described in Supplemental Experimental Procedures. To generate human LBs in vitro, a total of 1,140-10,140 cells per microwell at a ratio of 10:7:2 (human iPSC-tHE/iPSC-EC/iPSC-STM) were resuspended in a mixture of endothelial cell growth medium (EGM) and hepatocyte culture medium (HCM) (Cambrex, Baltimore, Md.) containing dexamethasone (0.1 µM; Sigma-Aldrich, St. Louis, Mo.), oncostatin M (10 ng/mL; R&D System, Minneapolis, Minn.), hepatocyte growth factor (HGF) (20 ng/mL, PromoKine), and SingleQuots (Lonza), and plated on either a 24-well plate or the Elplasia platform (co-developed by Kuraray, Inc.) in a 24-well, 6-well, or 1-well plate. The phase-contrast colony image shown in FIG. 3B (FIG. 3B) (top) was captured using a BioStation CT culture incubator, microscope, and digital imaging system (Nikon, Tokyo, Japan). The fluorescent time-lapse image shown in FIG. 3B (FIG. 3B) (bottom) was obtained with a Lightsheet Z.1 microscope (Zeiss, Germany). Generated human iPSC-LBs were collected by gentle pipetting and used for in vitro maturity assessment and in vivo transplantation experiments. As controls, the present inventors used five different human primary adult hepatocytes (lot numbers H768, H737, HC2-8, H4.1 and lot number: M00995, purchased from XenoTech, KS, USA and Veritas, Tokyo, Japan).

Quantification and Statistical Analysis

Data are expressed as the means±SEM or means±SD of the number of independent experiments specified in the figure legends. No randomization or blinding method was used in this study. The statistical significance of the amount of albumin produced was assessed by the non-parametric Mann-Whitney U test. Two-tailed p values of <0.05 were considered significant. For survival analysis, GraphPad Prism Software version 6.0 was used for statistical analysis.

Supplemental Information

Supplemental information includes supplemental experimental procedures and eight figures (FIGS. 5 to 12 (Figures S1-S8)).

REFERENCES

Asahina, K., Tsai, S. Y., Li, P., Ishii, M., Maxson, R. E., Jr., Sucov, H. M., and Tsukamoto, H. (2009). Mesenchymal origin of hepatic stellate cells, submesothelial cells, and perivascular mesenchymal cells during mouse liver development. Hepatology 49, 998-1011.

Asahina, K., Zhou, B., Pu, W. T., and Tsukamoto, H. (2011). Septum transversum-derived mesothelium gives rise to hepatic stellate cells and perivascular mesenchymal cells in developing mouse liver. Hepatology 53, 983-995.

Camp, J. G., Sekine, K., Gerber, T., Loeffler-Wirth, H., Binder, H., Gac, M., Kanton, S., Kageyama, J., Damm, G., Seehofer, D., et al. (2017). Multilineage communication regulates human liver bud development from pluripotency. Nature 546, 533-538.

Delgado, I., Carrasco, M., Cano, E., Carmona, R., Garcia-Carbonero, R., Marin-Gomez, L. M., Soria, B., Martin, F., Cano, D. A., Munoz-Chapuli, R., et al. (2014). GATA4 loss in the septum transversum mesenchyme promotes liver fibrosis in mice. Hepatology 59, 2358-2370.

Ding, Q., and Cowan, C. A. (2013). Liver in a dish. Cell Res 23, 1242-1243.

El Taghdouini, A., Sorensen, A. L., Reiner, A. H., Coll, M., Verhulst, S., Mannaerts, I., Oie, C. I., Smedsrod, B., Najimi, M., Sokal, E., et al. (2015). Genome-wide analysis of DNA methylation and gene expression patterns in purified, uncultured human liver cells and activated hepatic stellate cells. Oncotarget 6, 26729-26745.

Enosawa, S., Horikawa, R., Yamamoto, A., Sakamoto, S., Shigeta, T., Nosaka, S., Fujimoto, J., Nakazawa, A., Tanoue, A., Nakamura, K., et al. (2014). Hepatocyte transplantation using a living donor reduced graft in a baby with ornithine transcarbamylase deficiency: a novel source of hepatocytes. Liver Transpl 20, 391-393.

Horslen, S. P., and Fox, I. J. (2004). Hepatocyte transplantation. Transplantation 77, 1481-1486.

Huch, M., and Koo, B. K. (2015). Modeling mouse and human development using organoid cultures. Development 142, 3113-3125.

Iyer, D., Gambardella, L., Bernard, W. G., Serrano, F., Mascetti, V. L., Pedersen, R. A., Talasila, A., and Sinha, S. (2015). Robust derivation of epicardium and its differentiated smooth muscle cell progeny from human 460 pluripotent stem cells. Development 142, 1528-1541.

Jorns, C., Ellis, E. C., Nowak, G., Fischler, B., Nemeth, A., Strom, S. C., and Ericzon, B. G. (2012). Hepatocyte transplantation for inherited metabolic diseases of the liver. J Intern Med 272, 201-223.

Kajiwara, M., Aoi, T., Okita, K., Takahashi, R., Inoue, H., Takayama, N., Endo, H., Eto, K., Toguchida, J., Uemoto, S., et al. (2012). Donor-dependent variations in hepatic differentiation from human-induced pluripotent stem cells. Proc Natl Acad Sci U S A 109, 12538-12543.

Kolterud, A., Wandzioch, E., and Carlsson, L. (2004). Lhx2 is expressed in the septum transversum mesenchyme that becomes an integral part of the liver and the formation of these cells is independent of functional Lhx2. Gene Expr Patterns 4, 521-528.

Lancaster, M. A., and Knoblich, J. A. (2014). Organogenesis in a dish: modeling development and disease using organoid technologies. Science 345, 1247125.

Loh, K. M., Ang, L. T., Zhang, J., Kumar, V., Ang, J., Auyeong, J. Q., Lee, K. L., Choo, S. H., Lim, C. Y., Nichane, M., et al. (2014). Efficient endoderm induction from human pluripotent stem cells by logically directing signals controlling lineage bifurcations. Cell stem cell 14, 237-252.

Martin, I., Simmons, P. J., and Williams, D. F. (2014). Manufacturing challenges in regenerative medicine. Sci Transl Med 6, 232fs16.

Narazaki, G., Uosaki, H., Teranishi, M., Okita, K., Kim, B., Matsuoka, S., Yamanaka, S., and Yamashita, J. K. (2008). Directed and systematic differentiation of cardiovascular cells from mouse induced pluripotent stem cells. Circulation 118, 498-506.

Orlova, V. V., van den Hil, F. E., Petrus-Reurer, S., Drabsch, Y., Ten Dijke, P., and Mummery, C. L. (2014). Generation, expansion and functional analysis of endothelial cells and pericytes derived from human pluripotent stem cells. Nat Protoc 9, 1514-1531.

Patsch, C., Challet-Meylan, L., Thoma, E. C., Urich, E., Heckel, T., O'Sullivan, J. F., Grainger, S. J., Kapp, F. G., Sun, L., Christensen, K., et al. (2015). Generation of vascular endothelial and smooth muscle cells from human pluripotent stem cells. Nat Cell Biol 17, 994-1003.

Samuel, R., Daheron, L., Liao, S., Vardam, T., Kamoun, W. S., Batista, A., Buecker, C., Schafer, R., Han, X., Au, P., et al. (2013). Generation of functionally competent and durable engineered blood vessels from human induced pluripotent stem cells. Proc Natl Acad Sci U S A 110, 12774-12779.

Sasai, Y. (2013). Cytosystems dynamics in self-organization of tissue architecture. Nature 493, 318-326.

Si-Tayeb, K., Noto, F. K., Nagaoka, M., Li, J., Battle, M. A., Duris, C., North, P. E., Dalton, S., and Duncan, S. A. (2010). Highly efficient generation of human hepatocyte-like cells from induced pluripotent stem cells. Hepatology 51, 297-305.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci U S A 102, 15545-15550.

Takebe, T., Enomura, M., Yoshizawa, E., Kimura, M., Koike, H., Ueno, Y., Matsuzaki, T., Yamazaki, T., Toyohara, T., Osafune, K., et al. (2015). Vascularized and Complex Organ Buds from Diverse Tissues via Mesenchymal Cell-Driven Condensation. Cell Stem Cell 16, 556-565.

Takebe, T., Sekine, K., Enomura, M., Koike, H., Kimura, M., Ogaeri, T., Zhang, R. R., Ueno, Y, Zheng, Y. W., Koike, N., et al. (2013). Vascularized and functional human liver from an iPSC-derived organ bud transplant. Nature 499, 481-484.

Takebe, T., Zhang, R. R., Koike, H., Kimura, M., Yoshizawa, E., Enomura, M., Koike, N., Sekine, K., and Taniguchi, H. (2014). Generation of a vascularized and functional human liver from an iPSC-derived organ bud transplant. Nat Protoc 9, 396-409.

Witty, A. D., Mihic, A., Tam, R. Y., Fisher, S. A., Mikryukov, A., Shoichet, M. S., Li, R. K., Kattman, S. J., and Keller, G. (2014). Generation of the epicardial lineage from human pluripotent stem cells. Nat Biotechnol 32, 1026-1035.

Zaret, K. S. (2002). Regulatory phases of early liver development: paradigms of organogenesis. Nat Rev Genet 3, 499-512.

Details of Experimental Models and Subjects

Mice

In vitro generated LBs were collected and transplanted into a preformed cranial window or other indicated sites in non-obese diabetic/severe combined immunodeficient (NOD/SCID) mice (Sankyo Lab. Co., Tsukuba, Japan). The in vivo fate of the transplanted cells was monitored by intravital imaging using a Leica TCS SP8 confocal microscope (Leica Microsystems, Germany). For the in vivo functionalization studies, 8-week-old male NOG mice (~20-30 g body weight) were used (supplied by the Central Institute for Experimental Animals (CIEA), Kanagawa, Japan) (Hasegawa et al., 2011). For survival curves, albumin-TK-NOG mice (~20-30 g body weight) were used in this study (supplied by CIEA, Kanagawa, Japan). Ganciclovir (GCV, 50 mg/kg, i.p.), a drug that is not toxic to human or mouse tissues, was administered to induce tissue-specific ablation of transgenic liver parenchymal cells prior to transplantation, and $1 \times 10^7$ cell-equivalent iPSC-LBs per mouse were transplanted into the subscapular site of the kidney. The sample size was determined by the minimum size necessary to obtain a significant difference (P<0.05) at a power of 80% when there was a 30% change in the secreted albumin protein. The time point of euthanasia was randomly assigned. As for exclusion criteria for the transplant experiments, the present inventors pre-determined to exclude data from mice euthanized due to sickness, which are not related to transplantation. The mice were bred and maintained according to the Yokohama City University institutional guidelines for the use of laboratory animals.

Method Details

Human iPSC Culture and tHE Differentiation

Human iPSC lines (TkDA3-4, 1231A3, 1383D2, 1383D6 and Ff01) were kindly provided by Kyoto University and Tokyo University. 1231A3, 1383D2 and 1383D6 were established from ePBMC™ (Cellular Technology Limited, OH) at CiRA, Kyoto University. All iPSC lines were maintained on dishes in StemFit™ (Ajinomoto Co., Inc.); the dishes had been coated with Laminin 511 E8 fragment (iMatrix-511™, kindly provided by Nippi, Inc.) For in vitro and in vivo live imaging analysis, fluorescent protein knock-in reporters under the expression of adeno-associated virus integration site 1 (AAVS1::EGFP or mCherry) were used. To derive iPSC-tHEs, the present inventors developed a two-stage differentiation method (see, supplemental text). At the first stage, human iPSCs were seeded on an iMatrix-511-coated dish together with 10 μM ROCK Inhibitor Y-27632 (Wako, cat. no. 253-00513), and RPMI-1640 with 1% B27, 100 ng/ml human activin A (provided by Ajinomoto Inc.) and 50 ng/ml Wnt3a (R&D Systems) was used as the medium for 6 days. On the initial day of iPSC plating, 1 mM sodium butyrate (Sigma) was added. Successful endoderm specification was quantitatively assessed using Cerberus 1 ELISA kit (Dojin Kagaku, Kumamoto, Japan). Subsequently, human iPSC-derived endodermal cells were treated further with RPMI-1640 with 1% B27, 10 ng/ml human basic FGF, and 20 ng/ml human BMP4 for 2 days to derive a TBX3 and ADRA1B co-positive transitional hepatic endoderm population. Prior to adapting the described protocols for different iPSC clones, the present inventors strongly recommend that the respective specification markers of human iPSCs be examined at each time point of differentiation by immunostaining and gene expression studies in addition to careful microscopic observation, because successful liver bud generation is crucial for in vivo functional maturation. The use of human iPSC in this Example was approved by the Ethics Committee of the Yokohama City University.

Human iPSC-EC and STM Differentiation

For EC differentiation, human iPSCs were dissociated using Accutase and plated on Laminin 511 E8 fragment (iMatrix-511™, provided by Nippi, Inc.) at varying optimal densities (depending on the cell line) in StemFit™ (Ajinomoto Co., Inc.) with 10 μM ROCK inhibitor Y-27632. Next day, the medium was replaced with Priming Medium consisting of B27 medium [a 1:1 mixture of DMEM:F12 with 1% Glutamax and 1% B27 (all from Life Technologies)] containing 8 μM CHIR99021 (Tocris Bioscience) and 25 ng/ml BMP4 (R&D Systems). After additional three days, the priming medium was replaced with EC Induction Medium consisting of StemPro-34 SFM medium (Life Technologies) supplemented with 200 ng/ml VEGF (Life Technologies) and 2 μM forskolin (Sigma-Aldrich). The induction medium was renewed every day. At day 7 of differentiation, ECs were dissociated with 0.05% Trypsin and subjected to FACS analysis. iPSC-derived ECs are supposed to exhibit a typical endothelial morphology with localization of CD144/CD31 junctions. ECs were replated on 1 μg/cm$^2$ Fibronectin (Sigma-Aldrich)-coated dishes at a density of 50,000 cells/cm$^2$ in EC Expansion Medium consisting of StemPro-34 SFM supplemented with 50 ng/ml VEGF-A. EC 7 Expansion Medium was replaced every other day. For STM differentiation, human iPSCs were dissociated using Accutase, plated on Laminin 511 E8 fragment at 2000-8000 cells/cm$^2$ (depending on the cell line) in StemFit™ with 10 μM ROCK inhibitor Y-27632 and cultured for 4-6 days before induction. At the mesoderm induction stage, maintenance medium was replaced with mesoderm induction medium (1:1 mixture of DMEM:F12 with 1% Glutamax and 1% B27, the mixture further containing 8 μM CHIR99021 and 25 ng/ml BMP4; subsequently, 3 day-exposure to 2 ng/ml activin A and 10 ng/ml PDGFBB (R&D Systems) followed. After three days, the mesoderm induction medium was replaced with STM induction medium consisting of StmePro-34 SFM medium supplemented with 10 ng/ml FGF2 and 10 ng/ml PDGFBB, and cells were cultured for three days.

Elplasia™ Micro-Well Plate Manufacturing Process

Elplasia™ micro-well plate was industrially manufactured by a combination of two techniques; one for making a finely-structured metal mold and the other for transferring the structure accurately from the mold to a resin film. The production of such a finely-structured metal mold started with a process of master block preparation. The present inventors engraved micro-wells in a metal plate at equal distances by precise metal cutting work. Each micro-well was U-bottom shaped with an aperture diameter of about 500 μm and a depth of 400 μm. They were closely and triangularly arranged at 30 μm intervals in order that all the seeded cells would be distributed among individual micro-wells. The metal cutting work was followed by cutting into a square shape, polishing back side and giving a mold release treatment that improves detachment of resin from the metal mold. Through the above processes, a nickel plate was generated as a metal mold whose surface had many micro-pillars as inverted forms of micro-wells. Transfer of the micro-well structure from mold to resin film was conducted by using an internally developed transfer molding machine. Compared to the common injection molding machine, the developed molding machine significantly improves transfer accuracy especially in the part of high aspect ratio area such as the plate configuration of the present inventors (The 'aspect ratio' is the ratio of height to width of microstructure). In fact, the micro-well (depth: 400 μm, interval; 30 μm) of the present inventors has extremely high aspect ratio that is hard to transfer by the conventional molding machine. The present inventors attached the metal mold to the molding machine, and then applied melted polystyrene resin on the mold. Through several conditional optimizations including temperature, press weight and retention time, the present inventors finally obtained a resin film onto which micro-wells had been completely transferred. Trimmed film was welded with pre-made well plate frame without bottom, thereby completing Elplasia™ micro-well plate having a micro-well array in the bottom. Since there are about 320 micro-wells in every 1 cm$^2$ area, there are about 600 micro-wells/well in 24-well plate format, about 3,000 micro-wells/well in 6-well plate format, and about 20,000 micro-wells/plate in omni-plate format.

In vitro Imaging

Acquisition of phase-contrast colony images shown in FIG. 3B (FIG. 3B) (upper panel) was achieved using a BioStation CT culture incubator, a microscope and a digital imaging system (Nikon, Tokyo, Japan) preadjusted to optimize the auto-focus and cell image-tiling acquisition functions according to the instructions provided. Fluorescent time-lapse imaging shown in FIG. 3B (FIG. 3B) (lower panel) was imaged with Lightsheet Z.1 microscope (Zeiss, Germany).

Intravital Imaging

Tail vein injections of 1% tetramethylrhodamine-conjugated dextran (MW 2,000,000), fluorescein isothiocyanate-conjugated dextran (MW 2,000,000) and Texas Red-conjugated dextran (70,000 MW, neutral) were used to identify vessel lumens (all from Invitrogen, Carlsbad, Calif., USA). Host endothelial cells were visualized using intravenously injected Alexa647-conjugated mouse-specific CD31 (BD). Confocal image stacks were acquired for the implanted vessels and dextran.

Gene Expression Analysis qRT-PCR analyses were conducted as described previously (Takebe et al., 2013). For the microarray, total RNA was prepared using an RNeasy Mini Kit (Qiagen, Valencia, Calif.). RNA for gene expression profiling was hybridized on Whole Human Genome Agilent 4x44K v2 Oligonucleotide Microarray or Whole Human Genome Agilent 8x60K v2 Oligonucleotide (Agilent Technologies, Palo Alto, Calif.) according to the manufacturer's instructions. For control samples, human FLT (10 gwk or 22-40 gwk pool Fetal Liver Tissue), ILT (0 yr Infant Liver Tissue) and ALT (5 yrs, 30 yrs, 44 yrs or 55 yrs old Adult Liver Tissues) RNA samples were obtained from Biochain Institute (Hayward, Calif., USA) in addition to the above-descried human primary hepatocyte samples.

Hierarchical Clustering Analysis

Microarray data were processed using the GeneSpring standard protocol. Briefly, a signal intensity less than 1 was corrected to 1 (not detected), and then the 75th percentile shift normalization was conducted. After averaging the signal intensity within replicate spots, the batch effect, observed within different 8×60k v2 array chips (data not shown), was removed by Combat (Leek et al., 2012) with covariates of the same differentiation stages. When comparing with data from 4×44k v2 arrays, the present inventors conducted quantile normalization for robustly removing the difference among chips and the batch effects. To analyze the genome-wide differentiation state, the present inventors performed principal component analysis (PCA) (Le et al., 2008) using the scaled expression levels of protein-coding genes. Because the top principal component (PC) explained nearly 40% of the variance in all samples including 2-D cultured iPSCs and clinical specimens, the present inventors mainly used PC1 (FIG. 2D (FIG. 2D)). Unsupervised hierarchical clustering was performed with Pearson's correlation-based distance and average linkage method. To characterize development, we used the discovery lifemaps gene signatures acquired from http://discovery.lifemapsc.com/in-vivo-development/, 2015/4/8, and p-values from Gene Set Enrichment Analysis (GSEA) (Subramanian et al., 2005) were shown by heat map (FIG. 2H (FIG. 2H), comparison is described in this figure). Unless otherwise specified, data processing and analysis were performed using the statistical software R, version 3.0.1.

APRES (Aster Plot of Relative Enrichment Score) Algorithm

First, using hallmark gene sets in MSigDB version 5.0 (Subramanian et al., 2005), the present inventors conducted enrichment analysis which compares several different stages of tissue/cells with human fetal liver tissue (FLT, 10w). Calculated normalized enrichment score (NES) by GSEA software, was converted into modified NES (mNES) as follows: if NES>1, then mNES is NES; if −1<NES<1, then mNES is 1; otherwise, mNES is 1/|NES| This conversion allows the present inventors to compare NESs regardless of whether a target gene set was enriched in comparing sample or FLT. Next, the present inventors determined the width of each component of aster plot using the relative size of mNES calculated from comparison of human adult hepatocyte (AHEP 2D) versus FLT. For each tissue or cell type, relative mNES score was calculated as divided by mNES of AHEP 2D versus FLT, and this score was shown as the height of each component of aster plot. Finally, the present inventors multiplied the width and the height of the component, and then defined a total relative score by adding up the products. Total relative score is indicated at the center of the aster plot (FIG. 4F (FIG. 4F)).

ELISA

Blood samples were allowed to clot in a centrifuge tube (approximately 5 min) at room temperature, loosened from the sides of the tube and incubated at 4° C. (melting ice) for 20 min. Clotted blood was centrifuged for 10-15 min at 400 g at 4° C., and the serum fraction was removed with care being taken to exclude erythrocytes or clotted materials. Human CER1, ALB and AAT were measured in mouse serum samples using Human Cerberus 1 Quantification Kit (Dojin Kagaku, Kumamoto, Japan), Human Albumin ELISA Quantitation Kit (Bethyl Laboratories Inc., Montgomery, Tex., USA) and human alpha 1-antitrypsin ELISA Quantitation Kit (GenWay Biotech, Inc., San Diego, Calif., USA), according to the manufacturers' instructions. Blinded investigators performed all the ELISA experiments using in vitro culture supernatant or in vivo serum.

Data and Software Availability

The accession number of the microarray data reported in this Example will be updated once the data was uploaded via NCBI GEO.

Supplemental Text

Miniaturized Liver Bud Culture

After selecting a coating material (FIG. 5 (Fig. S1)), the present inventors first optimized the cell culture conditions by conducting mixture ratio- and dose-dependency studies. A mixing protocol for endothelial cells versus total cells was previously optimized based on efficient post-transplant vascularization (Takebe et al., 2014); however, a protocol for mesenchymal cells has not yet been determined. SEM analysis confirmed that 10%-1.4% (1/5-1/40 of endodermal cells) of the mesenchymal cell mixture enables reproducible LB generation (FIG. 6A (Figure S2A)), and subsequent gene expression analysis suggested that 2.8% (1/20 of endodermal cells) is the most efficient proportion for stable hepatic differentiation and tissue formation (FIG. 6B, C (Figure S2B, C)). The present inventors next performed a dose-reduction study to determine the minimal cell numbers for functional LB production (FIG. 6D-F (Figure S2D-F)). Cell number dependent LB size is shown in FIG. 6D (Figure S2D); LB size increased in a dose-dependent manner up to 4000 cells (over 6000 cells per microwell failed to form LB). An ELISA-based functional screening on long-term differentiated LB demonstrated that inclusion of 600 iPSC-tHE cells (total 1130 cells) per LB produced the highest level of human albumin compared to the inclusion of a larger or smaller number of iPSC-tHE cells (within the range from 150-1200 iPSC-tHE cells per LB) (FIG. 6F (Figure S2F)), as also confirmed by gene expression analysis of additional hepatic differentiation markers (FIG. 6D, E (Figure S2D, E)).

Selection of Highly Efficient Differentiation Protocols for Generating Hepatocyte-Like Cells The present inventors performed a number of 'reverse' screen experiments by comparing the morphology and functionality of differentiated liver buds using endodermal cells of multiple differentiation stages. A huge number of publications reported that each specific method by sequential addition of genes and proteins results in hepatocyte-like cell production; however, comparative analyses were seldom performed. Initially, 2-D based screens were performed to select three promising step-wise differentiation protocols (Kajiwara et al., 2012; Loh et al., 2014; Si-Tayeb et al., 2010) (FIG. 8A (Fig. S4A)). Then, the three major protocols were modified to become suitable for the feeder-free iPSC culture of the present inventors by optimizing cell density, cytokine exposure duration and basal media; as a result, differentiated cells in Protocol (Pr) 1 revealed minimized expression of pluripotent markers (OCT4 and 17 NANOG) and higher expression of hepatic markers (FOXA2, HNF4A, ALB and AFP) in definitive endoderm (DE) and mature hepatocyte-like (MHs) cells compared with Pr 2 and Pr 3 (FIG. 8B-E (Figure S4B-E)). These results were confirmed by human albumin secretion analysis by ELISA, which revealed that the secretion from MH of Pr 1 was approximately 2.5 times that of Pr 2 and Pr 3 (data not shown). Under Pr1 which amplifies Wnt signaling pathways, four different patient-derived iPSC clones were capable of differentiating functional hepatocyte-like cells in a highly reproducible manner (FIG. 4F (FIG. 4F)). To summarize, Wnt3A exposure in early endoderm specification is effective for generating functional hepatocyte-like cells in 2D culture.

Prospective Validation by Detecting CER1 Secretion

To identify prospective validation markers, transcriptome-based comparison of albumin high (good)/low (bad) MH and original DE cells was performed. The results suggested that better outcomes in 2D MH function correlates with the efficiency of DE specification (data not shown). Therefore, the present inventors hypothesized that successful hepatic maturation is largely dependent on the quality of early endoderm specification, particularly at the DE stage. In order to identify good DE markers, the present inventors compared the global gene expression profiles of good and bad DEs (as distinguished by eventual iPSC-MH functionality) and found that good DEs tend to express Cerberus 1 (CER1) at a much higher level (Iwashita et al., 2013). Cerberus 1 is a secretory and a known definitive endodermal maker, the level of which can be measured in a culture supernatant by ELISA. Thus, the present inventors found that detection of CER1 protein in culture media at day 6 is at least essential for the final ALB detection at day 20 (FIG. 4G (FIG. 4G)). This suggests that the secreted protein level at day 6 might be a potential requirement for hepatic functions after the completion of terminal differentiation.

SUPPLEMENTAL REFERENCES

Iwashita, H., Shiraki, N., Sakano, D., Ikegami, T., Shiga, M., Kume, K., and Kume, S. (2013). Secreted cerberus1 as a marker for quantification of definitive endoderm differentiation of the pluripotent stem cells. PLoS One 8, e64291.

Kajiwara, M., Aoi, T., Okita, K., Takahashi, R., Inoue, H., Takayama, N., Endo, H., Eto, K., Toguchida, J., Uemoto, S., et al. (2012). Donor-dependent variations in hepatic differentiation from human-induced pluripotent stem cells. Proc Natl Acad Sci USA 109, 12538-12543. Loh, K. M., Ang, L. T., Zhang, J., Kumar, V., Ang, J., Auyeong, J. Q., Lee, K. L., Choo, S. H., Lim, C. Y., Nichane, M., et al. (2014). Efficient endoderm induction from human pluripotent stem cells by logically directing signals controlling lineage bifurcations. Cell stem cell 14, 237-252.

Si-Tayeb, K., Noto, F. K., Nagaoka, M., Li, J., Battle, M. A., Duris, C., North, P. E., Dalton, S., and Duncan, S. A. (2010). Highly efficient generation of human hepatocyte-like cells from induced pluripotent stem cells. Hepatology 51, 297-305.

Takebe, T., Zhang, R. R., Koike, H., Kimura, M., Yoshizawa, E., Enomura, M., Koike, N., Sekine, K., and Taniguchi, H. (2014). Generation of a vascularized and functional human liver from an iPSC-derived organ bud transplant. Nat Protoc 9, 396-409.

Example 2

Directed differentiation of human iPSC into tHE was performed. Human iPSC culture and tHE differentiation were carried out in the same manner as described in Example 1 except for the following modifications.

Briefly, at the first stage, human iPSCs were seeded in iMtrix-511-coated dishes together with 10 μM ROCK inhibitor Y-27632 (Wako, Cat. No. 253-00513). After adding 1% B27, RPMI-1640 containing 100 ng/ml human activin A (kindly provided by Ajinomoto Co., Inc.) and 50 ng/ml Wnt3a (R&D Systems) was used as a medium for 6 days. By adding 2 μM CHIR99021 for 3 days instead of the above 50 ng/ml Wnt3a, cost reduction, xeno-free culture, and compatibility with the "Japanese Standards for Biological Ingredients" are achieved (FIGS. 13 and 14).

A schematic diagram of the protocol using CHIR99021 as an alternative for Wnt3a is shown in FIG. 13A. As a result of preliminary examination, a condition was selected such that 2 μM CHIR99021 is added for 3 out of the 6 days of DE directed differentiation.

Cell morphologies at each differentiation stage in the conventional method using Wnt3a and under the condition of adding 2 M CHIR99021 for 3 days are shown in FIG. 13B. No morphological differences are observed compared to the case of using Wnt3a.

Flow cytometry analyses of the positive ratio for CXCR4 (a DE marker) at the DE stage in the conventional method using Wnt3a and under the condition of adding 2 μM CHIR99021 for 3 days are shown in FIG. 13C. The positive ratio for CXCR4 in the latter case is comparable to the ratio in the case of using Wnt3a.

Expression analyses of individual differentiation markers by pPCR are shown in FIG. 13D. Marker expressions at individual stages that were obtained in the case of using DHIR d3 are comparable to those obtained in the case of using Wnt3a.

ELISA analysis of albumin secretion at the MH stage is shown in FIG. 13E. In multiple iPSC clones, albumin secretion in the case of using CHIR d3 tends to be comparable to, or higher than, the secretion in the case of using Wnt3a.

The cellular morphologies in MH (FIG. 14A) and LB (FIG. 14B) revealed no morphological differences as compared to the case of using Wnt3a.

Maker expression analyses in MH and LB by qPCR are shown in FIG. 14C. With respect to marker expression levels and ALB secretion levels, no significant difference was observed between Wnt3a and CHIR; there was observed no increase, either, in the expression of marker genes of other cell lineages (such as intestinal markers).

Example 3

EC extended culture was performed. Human iPSC-EC differentiation and STM differentiation were carried out in the same manner as described in Example 1, except for the following modifications.

For EC differentiation, human iPSCs were dissociated with Accutase and plated on Laminin 511 E8 fragment (iMatrix-511™, kindly provided by Nippi, Inc.) The medium was replaced with a priming medium containing a ROCK inhibitor. The priming medium is composed of 8 μM CHIR99021 (Tocris Bioscience)- and 25 ng/ml BMP4 (R&D Systems)-containing B27 medium [which is a 1:1 mixture of DMEM and F12, containing 1% Glutamax and 1% B27 (both from Life Technologies)]. This medium is exchanged with a ROCK-inhibitor-free priming medium on the next day.

Three days later, the priming medium was exchanged with an EC induction medium. This EC induction medium is composed of StemPro-34 SFM medium (Life Technologies) supplemented with 200 ng/ml VEGF (Life Technologies) and 2 μM forskolin (Sigma-Aldrich). The induction medium was renewed every day. At day 7 of differentiation, ECs were dissociated with 0.05% trypsin and subjected to FACS analysis. iPSC-derived ECs are supposed to exhibit a typical endothelial morphology with localization of CD144/CD31 junctions. ECs were re-plated on Laminin 511 E8 fragment (iMatrix-511™, kindly provided by Nippi, Inc.) in ROCK inhibitor-containing EC extended medium at a density of 50,000 cells/cm$^2$. The EC extended medium is composed of StemPro-34 SFM medium supplemented with 50 ng/ml VEGF-A.

On the next day, the medium was exchanged with Miracell™ EC (Takara Bio), which was then exchanged every other day.

By these procedures, it is possible to obtain highly CD31/CD144 co-positive cells in a more stable manner (FIGS. 15 and 16).

A revised version of directed differentiation protocol for iPS-derived vascular endothelial cells (iPS-EC) is shown in FIG. 15.

A schematic diagram of the directed differentiation protocol is shown in FIG. 16A.

Cellular morphologies from the conventional method and the revised method are shown in FIG. 16B. No morphological differences are observed.

Flow cytometry analyses of the positive ratio for EC markers in the conventional method and the revised method are shown in FIG. 16C.

The flow cytometry analyses in FIG. 16C are summarized in FIG. 16D. High CD31/CD144 positive ratios are obtained more stably in the revised method than in the conventional method.

Expression analyses of individual differentiation markers by qPCR are shown in FIG. 16E. Expression levels of EC markers are stable in the revised method even after passages.

Cell growth upon each passage is shown in FIG. 16F. Growth capacity after passages is high in the revised method compared to the conventional method.

These results show that even when the positive ratio was not stable in EC at P0, stable EC production was possible by re-seeding. Thus, the present inventors have succeeded in proliferating ECs after their completion.

All publications, patents and patent applications cited herein are incorporated herein by reference in their entirety.

INDUSTRIAL APPLICABILITY

The present invention is applicable to regenerative medicine and drug discovery screening.

The invention claimed is:

1. An organ bud prepared from vascular cells, mesenchymal cells and transitional hepatic endoderm cells that are HNF4A negative, TBX3 positive, and ADRA1B positive, wherein each of the vascular cell, the mesenchymal cell and the transitional hepatic endoderm cells has been induced from pluripotent stem cells.

2. The organ bud of claim 1, wherein the organ bud is liver bud.

3. The organ bud of claim 1, wherein the mesenchymal cell is CD166 positive and CD31 negative.

4. The organ bud of claim 1, wherein the mesenchymal cell is LHX2 positive and WT1 positive.

5. The organ bud of claim 4, wherein the transcriptions of FOXF1, HLX1, COL4A and ALCAM of the mesenchymal cell are activated and the mesenchymal cell is LHX2 positive, WT1 positive and MIIA positive.

6. The organ bud of claim 1, wherein the vascular cell is CD31 positive and CD144 positive.

7. The organ bud of claim 6, wherein expression of at least one gene selected from the group consisting of PECAM1, CDH5, KDR and CD34 of the vascular cell is increased relative to the corresponding expression in the pluripotent stem cell before directed differentiation.

8. The organ bud of claim 1, wherein LHX2 and WT1 co-positive cells obtained through the following steps are used as mesenchymal cells:
   a) culturing pluripotent stem cells in the presence of a β catenin activator and a factor belonging to the TGF-β superfamily,
   b) then culturing the cells in the presence of a PDGF receptor agonist and a factor belonging to the transforming growth factor β family, and
   c) further culturing the cells in the presence of an FGF.

9. The organ bud of claim 1, wherein CD166 positive but CD31 negative cells obtained through the following steps are used as mesenchymal cell:
   a) culturing pluripotent stem cells in the presence of a β catenin activator and a factor belonging to the TGF-β superfamily,
   b) then culturing the cells in the presence of a PDGF receptor agonist and a factor belonging to the transforming growth factor β family,
   c) further culturing the cells in the presence of an FGF, and
   d) subsequently conducting maintenance culture of the cells in a medium for mesenchymal cells.

10. The organ bud of claim 1, wherein CD31 and CD144 co-positive cells obtained through the following steps are used as vascular cells:
    a) culturing pluripotent stem cells in the presence of a ROCK inhibitor,
    b) then culturing the cells in the presence of a β catenin activator and a factor belonging to the TGF-β superfamily, and
    c) further culturing the cells in the presence of a vascular endothelial growth factor receptor (VEGFR) agonist and an adenylate cyclase activator.

11. A method of preparing the organ bud of claim 1, comprising culturing vascular cells, mesenchymal cells and transitional hepatic endoderm cells that are HNF4A negative, TBX3 positive, and ADRA1B positive in vitro, wherein each of the vascular cell, the mesenchymal cell and the transitional hepatic endoderm cells has been induced from pluripotent stem cells.

12. The method of claim 11, wherein the cells are cultured without using scaffold materials.

13. A method of preparing a tissue or an organ, comprising transplanting the organ bud of claim 1 into a non-human animal and differentiating the organ bud into a tissue or an organ.

14. A method of transplanting an organ bud, comprising transplanting the organ bud of claim 1 into a human or a non-human animal.

15. A method of regeneration or function recovery of a tissue or an organ, comprising transplanting the organ bud of claim 1 into a human or a non-human animal and differentiating the organ bud into a tissue or an organ.

16. A method of evaluating a drug, comprising using the organ bud of claim 1.

* * * * *